(12) United States Patent
Guo et al.

(10) Patent No.: US 12,383,576 B2
(45) Date of Patent: Aug. 12, 2025

(54) BIOLOGICAL POLYSACCHARIDE HAVING EFFECT OF PREVENTING AND TREATING HORMONE-DEPENDENT DERMATITIS AND APPLICATION THEREOF

(71) Applicant: ZHEJIANG GLLION BIOSCIENCE CO., LTD., Zhejiang (CN)

(72) Inventors: Hongliang Guo, Zhejiang (CN); Xiuyuan Zhuang, Zhejiang (CN); Binnian Zhu, Zhejiang (CN); Zhen Ye, Zhejiang (CN); Jiadi Wu, Zhejiang (CN); Xuan Wang, Zhejiang (CN); Xiaoyu Guo, Zhejiang (CN)

(73) Assignee: ZHEJIANG GLLION BIOSCIENCE CO., LTD., Zhejiang (CN)

( * ) Notice: Subject to any disclaimer, the term of this patent is extended or adjusted under 35 U.S.C. 154(b) by 861 days.

(21) Appl. No.: 17/612,841

(22) PCT Filed: May 21, 2020

(86) PCT No.: PCT/CN2020/091619
§ 371 (c)(1),
(2) Date: Nov. 19, 2021

(87) PCT Pub. No.: WO2020/233681
PCT Pub. Date: Nov. 26, 2020

(65) Prior Publication Data
US 2022/0241319 A1     Aug. 4, 2022

(30) Foreign Application Priority Data

May 21, 2019   (CN) .......................... 201910425981.7

(51) Int. Cl.
| | |
|---|---|
| *A61K 31/716* | (2006.01) |
| *A61K 9/00* | (2006.01) |
| *A61K 9/06* | (2006.01) |
| *A61K 45/06* | (2006.01) |
| *A61P 17/00* | (2006.01) |

(52) U.S. Cl.
CPC .......... *A61K 31/716* (2013.01); *A61K 9/0014* (2013.01); *A61K 9/06* (2013.01); *A61K 45/06* (2013.01); *A61P 17/00* (2018.01)

(58) Field of Classification Search
CPC .... A61K 31/716; A61K 9/0014; A61K 45/06; A61P 17/00
See application file for complete search history.

(56) References Cited

U.S. PATENT DOCUMENTS

| 2006/0247205 A1 | 11/2006 | Patchen et al. |
| 2008/0095731 A1 | 4/2008 | Mitra |
| 2008/0160043 A1 | 7/2008 | Kim et al. |
| 2016/0015734 A1 | 1/2016 | Kristiansen et al. |

FOREIGN PATENT DOCUMENTS

| CN | 102600494 A | 7/2012 |
| CN | 103981201 A | 8/2014 |
| CN | 106075120 A | 11/2016 |
| CN | 106075399 A | 11/2016 |
| KR | 19990076537 A | 10/1999 |
| WO | 0018411 A1 | 4/2000 |
| WO | 2012022478 A2 | 2/2012 |

OTHER PUBLICATIONS

English machine translation of CN 106075399 A, Nov. 9, 2016. Retreived from Google Patents (patents.google.com). (Year: 2016).*
Definition of prevent, Oxford English Dictionary Online, http://dictionary.oed.com/, accessed online Mar. 27, 2010, especially definition 9a. at p. 2. (Year: 2010).*
Nguyen et al., Autoimmunity Reviews, 2016, 15, p. 191-197. (Year: 2016).*
Google Patents English machine translation of CN 106075120 A, Nov. 9, 2016. Retreived from Google Patents (patents.google.com) . (Year: 2016).*
Laroche et al., Recent Patents on Biotechnology, 2007, 1, 59-73. (Year: 2007).*
Farage et al., British Journal of Dermatology, 2009, 160, p. 450-474. (Year: 2009).*
King, Guihui et al., "Facial Corticosteroid Addictive Dermatitis Related to Immunology Research", China medical cosmetology, No. 1, Dec. 31, 2015, pp. 132-134.
Wang, Haibo, "Non-official translation: Study on the Chemical Structure, Solution Behavior and Hypoglycemic Effect of Beta-Glucan in Oats", China Doctoral Dissertations Full-Text Database, No. 1, Mar. 15, 2005, E005-14.
Rouleau, Renée; "Skin Ingredient Spotlight: Beta Glucans (Works Wonders for Acne!)"; Dec. 11, 2009, pp. 1-2.
Jesenak, Milos et al.; "β-Glucan-based cream (containing pleuran isolated from pleurotus ostreatus) in supportive treatment of mild-to-moderate atopic dermatitis"; Journal of Dermatological Treatment, 2016, vol. 27, Issue 4, ISSN: 0954-6634 (Print) 1471-1753 (Online); pp. 1-5.
Mossman, Jake et al.; "Preventing and Treating Acne"; US Pharmacist; Apr. 17, 2006, vol. 4, 34-42; pp. 1-19.

* cited by examiner

*Primary Examiner* — Jonathan S Lau
(74) *Attorney, Agent, or Firm* — NKL Law; Bin Lu; Allen Xue

(57) ABSTRACT

A composition contains β-glucan and is used for preventing and/or treating hormone-dependent dermatitis, skin mucositis or other skin inflammatory diseases.

4 Claims, 14 Drawing Sheets

Yeast β-glucan + positive drug group 2

A

B

C

D

E

F

G

H

Before use    after 11 days of use

Before use    after 36 hours of use

Before use    after 5 days of use

BIOLOGICAL POLYSACCHARIDE HAVING EFFECT OF PREVENTING AND TREATING HORMONE-DEPENDENT DERMATITIS AND APPLICATION THEREOF

TECHNICAL FIELD

The present invention relates to the field of biotechnology, especially to a biological polysaccharide having effect of preventing and treating hormone-dependent dermatitis and application thereof.

BACKGROUND

Glucocorticoid is an extremely important regulatory molecule in the body, which plays an important role in regulating the development, growth, metabolism and immune function of the body, and is the most important regulatory hormone of the body's stress response, as well as is the most widely used and effective anti-inflammatory and immunosuppressive agent in clinical practice. In emergency or critical situations, glucocorticoids are often the first choice and have various effects such as anti-inflammatory, anti-toxic, anti-allergic, anti-shock, non-specific immunosuppressive and antipyretic effects, etc., which can prevent and stop the occurrence of immune inflammatory reactions and pathological immune reactions, and are effective in almost all types of allergic diseases.

However, there are significant risks associated with the long-term use of large amounts of glucocorticoids. Currently common hormone-dependent dermatitis is caused by the long-term incorrect use of topical drugs or cosmetics containing glucocorticoids. The hormone-dependent dermatitis has a rising trend in incidence recent years, and is stubborn and difficult to cure. At present, the commonly used treatment means stay on moisturizing, anti-inflammatory and anti-allergic and anti-infection treatment, which has a long treatment period, poor effect and easy to recur, and brings both physical and psychological harm in patients.

Therefore, there is an urgent need in the field to develop a drug that can effectively prevent and treat hormone-dependent dermatitis.

SUMMARY OF INVENTION

The purpose of the present invention is to provide a drug that can effectively prevent and treat hormone-dependent dermatitis.

Another purpose of the present invention is to provide a biopolysaccharide having efficacy for preventing and treating of hormone-dependent dermatitis and use thereof.

In a first aspect of the present invention, provided is a use of β-glucan in manufacture of a formulation or composition for preventing and/or treating hormone-dependent dermatitis.

In another preferred embodiment, the β-glucan is β-D-glucan.

In another preferred embodiment, the β-glucan is a β-1,3-glucan, preferably a β-1,3-glucan having β-1,6-branch.

In another preferred embodiment, the β-glucan has a structure of formula I (I)

[structure of formula I]

wherein l is an integer≥0, preferably 0-50, preferably 0-10, more preferably 0-3, more preferably 1-2, more preferably 1; in is an integer≥0, preferably 0-19, preferably 0-4, more preferably 0-1, more preferably 0; n is an integer≥3, preferably 30-60,000, more preferably 100-10,000.

In another preferred embodiment, the degree of branching (DB) of the β-glucan is 0.02-0.8, preferably 0.1-0.5, preferably 0.2-0.4.

In another preferred embodiment, the β-glucan comprising β-glucan having a triple helix steric structure.

In another preferred embodiment, the content of the β-glucan of triple helix steric structure is 80%, 90%, 95%, based on the total molar amount of β-glucan.

In another preferred embodiment, the β-1,3-main chain of the β-glucan is the main body of the triple helix steric structure.

In another preferred embodiment, the β-1,6-branch of the β-glucan is located outside the triple helix steric structure.

In another preferred embodiment, the β-glucan has a molecular weight≥2 kD, preferably 2 kD-40000 kD, more preferably 20 kD-20,000 kD.

In another preferred embodiment, the β-glucan may have a molecular weight of 5 kD-35000 kD; 10 kD-30,000 kD; 50 kD-25,000 kD; 100 kD-20,000 kD; 200 kD-18,000 kD; 400 kD-16,000 kD; 500 kD-14,000 kD; 1,000 kD-12,000 kD; 2000 kD-4000 kD; 3000 kD-5000 kD; 4000 kD-6000 kD; 5000 kD-7000 kD; 6000 kD-8000 kD; 7000 kD-9000 kD; or 8000 kD-10000 kD.

In another preferred embodiment, the β-glucan is selected from the group consisting of *Schizophyllum commune* β-glucan (schizophyllan, SPG), Lentinan β-glucan, *Sderoutium roifssii* β-glucan, *Grifola frondosa* β-glucan, *Pleurotus Ostreatus* polysaccharide, mushroom β-glucan, yeast β-glucan, oat β-glucan, and combinations thereof.

In another preferred embodiment, the β-glucan is *Schizophyllum commune* β-glucan.

In another preferred embodiment, the Lentinan β-glucan is a β-glucan with 2 β-1,6-branches for every 5 β-1,3-of the main chain, and 1 glucose residue per branch.

In another preferred embodiment, the β-glucan has a purity of ≥70%, preferably ≥90%, more preferably ≥95%, more preferably ≥99%.

In another preferred embodiment, the β-glucan has good stability.

In another preferred embodiment, the β-glucan is in solid form or in liquid form, such as β-glucan solid granules or powder, or β-glucan aqueous solution.

In another preferred embodiment, the β-glucan granules or powder have a particle size≤20 mm, preferably 0.001-10 mm, more preferably 0.01-5 mm, more preferably 0.1-2 mm.

In another preferred embodiment, the β-glucan is a completely water-soluble β-glucan.

In another preferred embodiment, the β-glucan (granules or powder) has good water solubility and/or naturally soluble property.

In another preferred embodiment, the β-glucan (granules or powder) has a solubility in water (100 g) at 25° C. of ≥0.0001 g, preferably 0.01-50 g, more preferably 0.1-10 g.

In another preferred embodiment, the solubility of the β-glucan (granules or powder) in water (100 g) at 25° C. may be 0.1-100 g; 0.2-90 g; 0.5-80 g; 1-50 g; or, the solubility may be 0.1-0.3 g; 0.2-0.4 g; 0.3-0.5 g; 0.4-0.6 g; 0.5-0.7 g; 0.6-0.8 g; 0.7-0.9 g; 0.8-1 g; or 1-3 g; 2-4 g; 3-5 g; 4-6 g; 5-7 g; 6-8 g; 7-9 g; 8-10 g.

In another preferred embodiment, the β-glucan solution is a solution of β-glucan in water, i.e. a β-glucan aqueous solution.

In another preferred embodiment, the β-glucan (aqueous) solution has a high viscosity; preferably, the viscosity (at 25° C.) of the β-glucan aqueous solution with a mass concentration of 0.5% is ≥40 mPa·s, more preferably 100-10000 mPa·s, more preferably 500-2000 mPa·s.

In another preferred embodiment, the viscosity (25° C.) of the β-glucan solution aqueous with mass concentration of 0.5% may be 50-10000 mPa·s; 100-9000 mPa·s; 200-8000 mPa·s; 300-7000 mPa·s; 400-6000 mPa·s; 450-5000 mPa·s; 500-5000 mPa·s; 550-4000 mPa·s; 600-3000 mPa·s; 650-2000 mPa·s; 700-1500 mPa·s.

In another preferred embodiment, the β-glucan aqueous solution with a mass concentration of 1% has high clarity or high light transmittance, the β-glucan aqueous solution with a mass concentration of 1% has a light transmission of ≥50%, preferably ≥80%, preferably ≥85%, more preferably ≥95%.

In another preferred embodiment, the β-glucan solution has good stability.

In another preferred embodiment, the preventing and/or treating hormone-dependent dermatitis comprises: preventing the development or recurrence of hormone-dependent dermatitis, improving or relieving the symptoms of hormone-dependent dermatitis, accelerating the subsiding or healing of hormone-dependent dermatitis, improving the residual scarring of hormone-dependent dermatitis, or accelerating the subsiding of hormone-dependent dermatitis scars.

In another preferred embodiment, the preventing and/or treating hormone-dependent dermatitis is the prevention of recurrence of hormone-dependent dermatitis.

In another preferred embodiment, the treating hormone dependent dermatitis comprises inhibiting the side effects of hormone-dependent dermatitis treatment drugs.

In another preferred embodiment, the β-glucan is used to inhibit the side effects of hormone-dependent dermatitis treatment drugs.

In another preferred embodiment, the side effects include inflammation, edema and burning, or pain.

In another preferred embodiment, the "hormone-dependent dermatitis" refers to dermatitis caused by long-term repeated improper topical application of hormone, clinical presentation thereof is characterized by epidermal and dermal thinning, hypopigmentation or hyperpigmentation, vascular exposure, rosacea-like or acne-like dermatitis, folliculitis, having hormone-dependence and rebound phenomenon, also known as hormonal face.

In another preferred embodiment, symptoms of the hormone-dependent dermatitis comprising the group consisting of: skin itching, burning, pain, dryness, desquamation, tightness, flushing of facial skin, recurrent erythema, papules, skin atrophy and thinning, capillary dilation, acne breakouts, rosacea-like changes, hyperpigmentation or depigmentation, atrophic lines on facial skin, or folliculitis pustules and the like.

In another preferred embodiment, the formulation or composition comprising (a) β-glucan; and optionally (b) a pharmaceutically, cosmetically, or device acceptable carrier or excipient.

In a further preferred embodiment, the formulation or composition comprising (a) *Schizophyllum commune* β-glucan; and optionally (b) a pharmaceutically, cosmetically, or device acceptable carrier or excipient.

In another preferred embodiment, the formulation or composition contains 0.0001-99 wt %, preferably 0.001-90 wt %, more preferably 0.01-50 wt %, more preferably 0.05-10 wt % of β-glucan, based on the total weight of the formulation or composition.

In another preferred embodiment, the β-glucan in the formulation or composition has a mass concentration of ≥1 μg/mL, specifically may be 1 μg/mL-200 mg/mL, or 1 μg/mL-5 mg/mL, or 1 μg/mL-1 mg/mL.

In another preferred embodiment, the formulation or composition is further used for enhancing skin immunity or active defense function.

In another preferred embodiment, the formulation or composition is further used for preventing and/or treating skin mucositis or other skin inflammatory diseases.

In another preferred embodiment, the dosage form of the composition or formulation is a solid dosage form, a semi-solid dosage form, or a liquid dosage form, such as a solution, gel, cream, lotion, etc.

In another preferred embodiment, the composition is a pharmaceutical composition or a cosmetic composition, preferably in a topical dosage form.

In another preferred embodiment, the formulation is a topical formulation or transdermal formulation (e.g. topical solution, ointment, patch, etc.).

In another preferred embodiment, the formulation or composition comprises a cosmetic, a food, a medical device or a drug, specifically the cosmetic may be an efficacious cosmetic.

A second aspect of the present invention provides a formulation, wherein the formulation comprising β-glucan.

In another preferred embodiment, the β-glucan is selected from the group consisting of *Schizophyllum commune* β-glucan, Lentinan β-glucan, Sderoutium roifssii β-glucan, *Grifola frondosa* β-glucan, *Pleurotus Ostreatus* polysaccharide, mushroom β-glucan, yeast β-glucan, oat β-glucan, and combinations thereof.

In another preferred embodiment, the β-glucan is *Schizophyllum commune* β-glucan.

In another preferred embodiment, the β-glucan is a completely water-soluble β-glucan.

In another preferred embodiment, the formulation is *Schizophyllum commune* β-glucan and the β-glucan has good water solubility, naturally soluble property and/or redissolve ability.

In another preferred embodiment, the β-glucan in the formulation is in solid form or liquid form.

In another preferred embodiment, the formulation comprises a β-glucan aqueous solution, the mass concentration of the β-glucan is 0.0001-50 wt %, preferably 0.02-10 wt %, more preferably 0.05-5 wt %, based on total weight of the β-glucan aqueous solution.

In another preferred embodiment, the formulation contains≥80 wt %, preferably ≥90 wt %, more preferably ≥95 wt %, more preferably ≥99 wt %, more preferably ≥99.5 wt % of the β-glucan aqueous solution, based on total weight of the formulation.

In another preferred embodiment, the β-glucan in the formulation has one or more characteristics selected from the group consisting of:
(1) the β-glucan having a purity of ≥70%, preferably ≥90%, more preferably ≥95%, more preferably ≥99%;
(2) the β-glucan has good water solubility, is easy to be redissolved and/or has good natural solubility;
(3) the β-glucan (granules or powder) has a solubility of ≥0.0001 g/100 g water at 25° C., preferably 0.01-50 g/100 g water, more preferably 0.1-10 g/100 g water.
(4) the β-glucan aqueous solution has high clarity or high light transmittance; preferably, the β-glucan aqueous solution with a mass concentration of 1% has a light transmittance of ≥50%, preferably ≥80%, preferably ≥85%, more preferably ≥95%;
(5) the β-glucan solution has a high viscosity; preferably, the viscosity of the β-glucan aqueous solution (at 25° C.) of 0.5% by mass is ≥40 mPa·s, more preferably 100-10000, more preferably 600-2000 mPa·s;
(6) the β-glucan aqueous solution has good stability; and/or
(7) the molecular weight of the β-glucan is ≥2 kD, more preferably 2 kD-40000 kD, more preferably 20 kD-20000 kD.

In another preferred embodiment, the formulation comprising: (a) β-glucan; and (b) a pharmaceutically, cosmetically, or device acceptable carrier or excipient.

In another preferred embodiment, the formulation contains 0.0001-99 wt %, preferably 0.001-90 wt %, more preferably 0.01-50 wt %, more preferably 0.05-10 wt % of β-glucan, based on total weight of the formulation.

In another preferred embodiment, the formulation further comprising (c) a second active ingredient which is active ingredient different from the β-glucan and for treating hormone-dependent dermatitis, or active ingredient for treating skin mucositis or other skin diseases.

In another preferred embodiment, the active ingredient for treating hormone-dependent dermatitis is selected from the group consisting of moisturizing agents, skin barrier repairing ingredients, topical non-hormonal immunosuppressants, antihistamines, antiallergic agents, antibacterial agents, and antibiotics, etc., specifically, such as glycerin, allantoin, hyaluronic acid, polyglutamic acid, aloe vera gel, silicone oil, horse oil, lanolin oil, ceramide, epidermal growth factor, tacrolimus, pimecrolimus, Loratadine, ebastine, boric acid, benzalkonium chloride, erythromycin, etc., or any combinations thereof.

In another preferred embodiment, the active ingredient for treating hormone-dependent dermatitis is selected from the following group of traditional Chinese medicines and their extracts: class of heat-clearing and removing toxin, class of heat-clearing, draining dampness and removing toxin, class of heat-clearing, cooling blood and removing toxin, class of blood-activating, class of resolving stasis and dissipating mass, class of harmonizing and conception vessels, Wind-damp-dispellings, and combinations thereof; specifically, for example, Atractylodes, Pinellia, Bupleurum, tangerine peel, Red Peony, Rhubarb, Rehmannia, Poria, Licorice, *cassia* twig, Coptis, Scutellaria, Centella *asiatica*, Turmeric, honeysuckle, forsythia, peony root/bark, burdock, loquat leaves, dandelion, *ginseng*, Cortex Mori, yam, raw hawthorn, black plum, wild *chrysanthemum*, raw *coix* seed, Fructus *Gardeniae* Praeparatus, fructus *aurantii* immaturus, bamboo shavings, Notopterygium root, radix angelicae pubescentis, Saposhnikoviae Radix, *gentiana macrophylla*, radix clematidis, cortex acanthopanacis, and combinations thereof.

In another preferred embodiment, the active ingredients for treating skin mucositis or other skin diseases are selected from the group consisting of antihistamines, antibiotics, antifungal agents, hormones, immunosuppressants, vitamins, vitamin A acid, cleansers, protectants, antipruritic agents, keratin promoter, keratin exfoliator, astringent, corrodent, antimicrobial, antifungal, antiviral, insecticide, shading agent, decolorizer, or combinations thereof; specifically, for example, chlorpheniramine, loratadine, astemizole, ranitidine, dexamethasone, methylprednisolone, nystatin, ketoconazole, clotrimazole, 5-fluorocytosine, adapalene, glycosides of tripterygium wilfordii, chloroquine, iodine tincture, calamine lotion, or combinations thereof.

In another preferred embodiment, the formulation is used for the prevention and/or treatment of hormone-dependent dermatitis.

The third aspect of the present invention provides a composition product, comprising:
(1) a first pharmaceutical composition, comprising (a) a first active ingredient, and the first active ingredient is β-glucan; and (b) a pharmaceutically acceptable carrier; and
(2) a second pharmaceutical composition, which is a therapeutic drug for hormone-dependent dermatitis, or therapeutic drug for skin mucositis or other skin diseases.

In another preferred embodiment, the first pharmaceutical composition contains 0.0001-99 wt %, preferably 0.001-90 wt %, more preferably 0.01-50 wt %, more preferably 0.05-10 wt % of β-glucan, based on total weight of the first pharmaceutical composition.

In another preferred embodiment, the β-glucan is selected from the group consisting of *Schizophyllum commune* β-glucan, Lentinan β -glucan, Sderoutium roifssii β-glucan, *Grifola frondosa* β-glucan, *Pleurotus Ostreatus* polysaccharide, mushroom β-glucan, yeast β-glucan, oat β-glucan, and combinations thereof.

In another preferred embodiment, the β-glucan is *Schizophyllum commune* β-glucan.

In another preferred embodiment, the formulation further comprising (a) a second active ingredient which is active ingredient different from the β-glucan and for treating hormone-dependent dermatitis, and (b) pharmaceutically, cosmetically, or device acceptable carriers or excipients.

In another preferred embodiment, the active ingredient for treating hormone-dependent dermatitis is selected from the group consisting of moisturizing agents, skin barrier repairing ingredients, topical non-hormonal immunosuppressants, antihistamines, antiallergic agents, antibacterial agents, and antibiotics, etc., specifically, such as glycerin, allantoin, hyaluronic acid, polyglutamic acid, aloe vera gel, silicone oil, horse oil, lanolin oil, ceramide, epidermal growth factor, tacrolimus, pimecrolimus, Loratadine, ebastine, boric acid, benzalkonium chloride, erythromycin, etc., or any combinations thereof.

In another preferred embodiment, the therapeutic drug for hormone-dependent dermatitis is selected from the following group of traditional Chinese medicines and their extracts: class of heat-clearing and removing toxin, class of heat-clearing, draining dampness and removing toxin, class of heat-clearing, cooling blood and removing toxin, class of blood-activating, class of resolving stasis and dissipating mass, class of harmonizing and conception vessels, Wind-damp-dispellings, and combinations thereof; specifically, for example, Atractylodes, Pinellia, Bupleurum, tangerine peel, Red Peony, Rhubarb, Rehmannia, Poria, Licorice, cassia twig, Coptis, Scutellaria, Centella asiatica, Turmeric, honeysuckle, forsythia, peony root/bark, burdock, loquat leaves, dandelion, ginseng, Cortex Mori, yam, raw hawthorn, black plum, wild chrysanthemum, raw coix seed, Fructus Gardeniae Praeparatus, fructus aurantii immaturus, bamboo shavings, Notopterygium root, radix angelicae pubescentis, Saposhnikoviae Radix, gentiana macrophylla, radix clematidis, cortex acanthopanacis, and combinations thereof.

In another preferred embodiment, the therapeutic drug for skin mucositis or other skin diseases are selected from the group consisting of antihistamines, antibiotics, antifungal agents, hormones, immunosuppressants, vitamins, vitamin A acid, cleansers, protectants, antipruritic agents, keratin promoter, keratin exfoliator, astringent, corrodent, antimicrobial, antifungal, antiviral, insecticide, shading agent, decolorizer, or combinations thereof; specifically, for example, chlorpheniramine, loratadine, astemizole, ranitidine, dexamethasone, methylprednisolone, nystatin, ketoconazole, clotrimazole, 5-fluorocytosine, adapalene, glycosides of tripterygium wilfordii, chloroquine, iodine tincture, calamine lotion, or combinations thereof.

In another preferred embodiment, the first pharmaceutical composition and the second pharmaceutical composition are each separate, or combined in one.

In a further preferred embodiment, the composition product is for the treatment and/or prevention of hormone-dependent dermatitis.

In a further preferred embodiment, the composition product is a cosmetic or pharmaceutical product.

In another preferred embodiment, the recurrence rate and side effects of treatment with the composition product are lower than the recurrence rate and side effects of treatment with the second pharmaceutical composition alone.

A fourth aspect of the present invention provides a method for preventing and/or treating hormone-dependent dermatitis comprising a step of (a) administering β-glucan to a subject in need thereof.

In another preferred embodiment, the β-glucan is selected from the group consisting of Schizophyllum commune β-glucan, Lentinan β -glucan, Sderoutium roifssii β-glucan, Grifola frondosa β-glucan, Pleurotus Ostreatus polysaccharide, mushroom β-glucan, yeast β-glucan, oat β-glucan, and combinations thereof.

In another preferred embodiment, the β-glucan is Schizophyllum commune β-glucan.

In another preferred embodiment, the subject comprises a patient with hormone-dependent dermatitis, or a normal population.

It should be understood that within the scope of the present invention, the above-described technical features of the present invention and the technical features described in detail below (e.g., embodiments) may be combined with each other to constitute a new or preferred technical solution. Limited by space, it will not be repeated here.

DETAILED DESCRIPTION OF THE INVENTION

Figure 1:
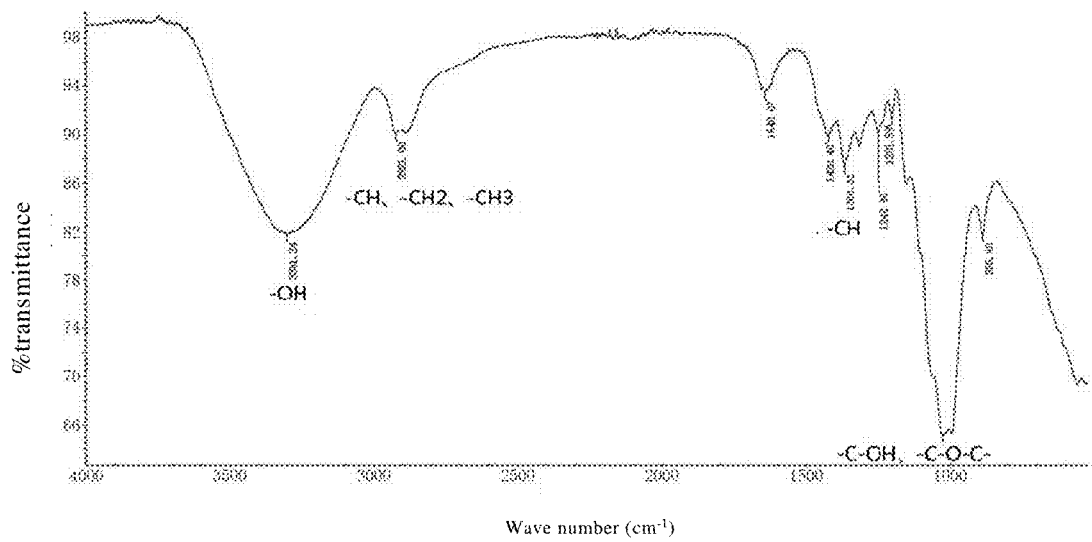
FIG. 1 shows the Fourier transform infrared (FTIR) spectra of β-glucan of Schizophyllum commune prepared in Example 1.

After extensive and deep research, the present inventors unexpectedly discovered for the first time that β-glucan, especially β-glucan with naturally soluble property, high molecular weight and high viscosity (e.g., *Schizophyllum commune* β-glucan), can be very effective in preventing and/or treating hormone-dependent dermatitis. Experiments have shown that *Schizophyllum commune* β-glucan has the effects of significantly alleviating and improving hormone-dependent dermatitis, effectively controlling the occurrence of hormone-dependent dermatitis, and accelerating healing and/or regression of hormone-dependent dermatitis. At the same time, *Schizophyllum commune* β-glucan can xiahenhance the active defense function of skin, activate the natural immunity of skin, resist to bacteria, eliminate inflammation and repair skin, and treat or prevent skin mucositis or other skin inflammatory diseases. On this basis, the present invention was completed.

Terms

Unless otherwise defined, all technical and scientific terms used herein have the same meaning as commonly understood by those skilled in the art.

As used herein, when used in reference to a specifically value, the term "about" means that the value can vary from the enumerated value by no more than 1%. For example, as used herein, the expression "about 100" includes all values between 99 and 101 (e.g., 99.1, 99.2, 99.3, 99.4, etc.).

As used herein, the terms "contain" or "include (comprise)" can be open-ended, semi-closed, and closed-ended. In other words, the term also includes "consisting essentially of", or "consisting of".

As used herein, the term "fully water soluble" refers to the β-glucan in solid form that can be fully soluble in water to form an aqueous solution of β-glucan, i.e., the solubility of β-glucan in 100 g of water at 25° C. is ≥0.0001 g, preferably 0.01-50 g, more preferably 0.1 g-10 g.

As used herein, the term "naturally soluble property" refers to a property that the β-glucan in natural state, owned by it self, can completely dissolved in water to form an aqueous solution. The term "β-glucan in natural state" refers to β-glucan produced by natural methods (e.g. biofermentation) without any chemical modification and without any physical and/or chemical and/or biological method of breaking its long chain to reduce its molecular mass. In another preferred embodiment, the β-glucan of the present invention is a β-glucan in natural state.

Hormone Dependent Dermatitis

The term "hormone-dependent dermatitis" refers to dermatitis caused by long-term repeated improper topical hormone application, clinical presentation thereof is characterized by epidermal and dermal thinning, hypopigmentation or hyperpigmentation, vascular exposure, rosacea-like or acne-like dermatitis, folliculitis, hormone-dependence and rebound phenomenon, also known as hormonal face. Specifically, Epidermal and dermal thinning: Long-term topical application of hormones topically can lead to thinning of the stratum corneum due to reduced granule formation, thinning of the dermis due to changes in the elasticity of glycoproteins and proteoglycans that weaken the interprotofibrillary adhesion of collagen and reduce collagen synthesis.

Hypopigmentation and hyperpigmentation: due to decreased number of layers of the stratum corneum, less melanin migrates to the keratin-forming cells, causing hypopigmentation. Hyperpigmentation may be related to the activation of melanocytes by glucocorticoids to regenerate pigment.

Vascular exposure: vessels can be widen due to the weakened adhesion between collagen fibers in the vessel wall and dermal collagen disappears leading to exposure of surface vessels.

Rosacea-like and acne-like dermatitis: in hormone-induced rosacea-like lesions, there is a significant increase in the density of *Demodex folliculorum*, which close the follicular sebaceous gland outlet and cause an inflammatory response or allergy. Potent hormones can also cause sebaceous gland hyperplasia, resulting in a characteristic rosacea-like rash. Hormones can cause degeneration of the epithelium of hair follicles, resulting in blocked outlets and occurance of an acne-like rash or aggravation of existing acne.

Folliculitis: localized hair follicle infections and aggravation of pre-existing folliculitis may occur due to the immunosuppressive effect of hormones.

Hormone dependence and rebound phenomenon: The anti-inflammatory properties of hormones can inhibit the development of papules and reduce itching, and result in vasoconstriction and disappearance of erythema. However, hormones cannot eliminate the cause of the disease and can often cause aggravation of the original disease after withdrawal, which can manifest as rebound phenomenon such as inflammatory edema, redness, burning, discomfort, and acute pustular rash. This phenomenon often occurs 2 to 10 days after withdrawal of hormone and lasts for a few days or about 3 weeks. The rebound phenomenon causes patients to continue topical hormone application, resulting in hormone dependence.

The general diagnosis of hormone-dependent dermatitis is as follows:
1. Long-term repeated topical application of glucocorticosteroids for >1 month, with the phenomenon that conditions can be cured during the application, and recur when withdrawal.
2. The primary skin disease has been cured, and then repeatedly appear obvious erythema, papules, pustules, loss of skin lines, desquamation and other dermatitis manifestations.
3. Most often occurs on in the thin and tender skin areas such as face, vulva, folds and the like.
4. Long-term drug application leaves symptoms such as hyperpigmentation (hypopigmentation), striae atrophicae, capillary dilation, hirsutism, pustules, etc., accompanied by stinging and burning sensations.

β-Glucan

β-glucan is a natural polysaccharide, and quite a variety kinds of β-glucan can be found in natural environments, usually in the cell walls of specific species of bacteria, yeasts, fungi (*Ganoderma lucidum*), and also in the envelope of seeds of higher plants. There are two main methods to produce β-glucan, one is directly extraction from cereals such as oats or fruiting body fungus such as mushrooms; the other is obtainment of β-glucan through liquid fermentation of fungi or bacteria and extracting process of the fermentation broth.

As used herein, the terms "β-glucan of the present invention" and "biopolysaccharide of the present invention" are used interchangeably and refer primarily to the β-glucan described in the first aspect of the present invention, the β-glucan is selected from the group consisting of *Schizophyllum commune* β-glucan, Lentinan β -glucan, Sderoutium roifssii β-glucan, *Grifola frondosa* β-glucan, *Pleurotus Ostreatus* polysaccharide, mushroom β-glucan, yeast β-glucan, oat β-glucan, and combinations thereof, preferably, *Schizophyllum commune* β-glucan.

As used herein, "*Schizophyllum commune* β-glucan (or schizophyllan, or SPG)" refers to β-glucan derived from *Schizophyllum commune*.

In another preferred embodiment, the β-glucan has a structure of Formula I.

In another preferred embodiment, the β-glucan has a molecular weight≥2 kD, preferably 2 kD-40000 kD, more preferably 20 kD-20,000 kD.

In another preferred embodiment, the β-glucan may have a molecular weight of 5 kD-35000 kD; 10 kD-30,000 kD; 50 kD-25,000 kD; 100 kD-20,000 kD; 200 kD-18,000 kD; 400 kD-16,000 kD; 500 kD-14,000 kD; 1,000 kD-12,000 kD; 2000 kD-4000 kD; 3000 kD-5000 kD; 4000 kD-6000 kD; 5000 kD-7000 kD; 6000 kD-8000 kD; 7000 kD-9000 kD; or 8000 kD-10000 kD.

In another preferred embodiment, the β-glucan has a purity of ≥70%, preferably ≥90%, more preferably ≥95%, more preferably ≥99%.

In another preferred embodiment, the β-glucan has good stability.

In another preferred embodiment, the β-glucan is in solid form or in liquid form, such as β-glucan solid granules or powder, or β-glucan aqueous solution.

In another preferred embodiment, the β-glucan granules or powder have a particle size≤20 mm, preferably 0.001-10 mm, preferably 0.01-5 mm, preferably 0.1-2 mm.

In another preferred embodiment, the β-glucan (granules or powder) has good water solubility and/or naturally soluble property.

In another preferred embodiment, the β-glucan (granules or powder) has a solubility of ≥0.0001 g in water (100 g) at 25° C., preferably 0.01-50 g, more preferably 0.1-10 g.

In another preferred embodiment, the solubility of the β-glucan (granules or powder) in water (100 g) at 25° C. may be 0.1-100 g; 0.2-90 g; 0.5-80 g; 1-50 g; or, the solubility may be 0.1-0.3 g; 0.2-0.4 g; 0.3-0.5 g; 0.4-0.6 g; 0.5-0.7 g; 0.6-0.8 g; 0.7-0.9 g; 0.8-1 g; or 1-3 g; 2-4 g; 3-5 g; 4-6 g; 5-7 g; 6-8 g; 7-9 g; 8-10 g.

In another preferred embodiment, the β-glucan solution is a solution of β-glucan in water, i.e. a β-glucan aqueous solution.

In another preferred embodiment, the β-glucan (aqueous) solution is viscous; preferably, the viscosity of the 0.5% by mass β-glucan aqueous solution (at 25° C.) is ≥40 mPa·s, more preferably 100-10000 mPa·s, more preferably 500-2000 mPa·s.

In another preferred embodiment, the viscosity of the 0.5% by mass β-glucan aqueous solution (25° C.) can be 50-10000 mPa·s; 100-9000 mPa·s; 200-8000 mPa·s; 300-7000 mPa·s; 400-6000 mPa·s; 450-5000 mPa·s; 500-5000 mPa·s; 550-4000 mPa·s; 600-3000 mPa·s; 650-2000 mPa·s; 700-1500 mPa·s.

In another preferred embodiment, the 1% by mass β-glucan aqueous solution has high clarity or high light transmittance, the 1% by mass β-glucan aqueous solution has a light transmittance of ≥50%, preferably ≥80%, preferably ≥85%, more preferably ≥95%.

In another preferred embodiment, the β-glucan solution has good stability.

In another preferred embodiment, the β-glucan is derived from higher plants or from various bacteria or bacteria, fungus.

Examples of the present invention specifically take the fermentation product of the *Schizophyllum commune* as an example, but it is not limited thereto.

The β-glucan of the present invention is an efficacious ingredient for the prevention and treatment of hormone-dependent dermatitis. On the one hand, the β-glucan enhances the resistance of normal skin, thus effectively preventing the infestation of external pathogenic microorganisms; on the other hand, for skin inflammation caused by bacterial infection and the like, the β-glucan can prevent the damage resulted from excessive inflammation, and also promote the repair of damaged skin. The β-glucan of the present invention also enhances the active defense function of the skin and stimulates the cellular basic immune function, and prevents excessive inflammation, has a two-way immune regulation function, and will not harm the patient's skin or develop drug resistant.

Formulation or Composition

The present invention provides a formulation or composition for preventing and/or treating of hormone-dependent dermatitis, the formulation or composition comprises (a) β-glucan; and optionally (b) a pharmaceutically, cosmetically, or device acceptable carriers or excipients.

In another preferred embodiment, the formulation or composition comprises (a) *Schizophyllum commune* β-glucan; and optionally (b) a pharmaceutically, cosmetically, or device acceptable carriers or excipients.

In another preferred embodiment, the formulation or composition contains 0.0001-99 wt %, preferably 0.001-90 wt %, more preferably 0.01-50 wt %, more preferably 0.05-10 wt % of β-glucan (Preferably *Schizophyllum commune* β-glucan), based on total weight of the formulation or composition.

In another preferred embodiment, the β-glucan in the formulation or composition has a mass concentration of ≥1 μg/mL, specifically may be 1 μg/mL-200 mg/mL, or 1 μg/mL-5 mg/mL, or 1 μg/mL-1 mg/mL.

In another preferred embodiment, the formulation contains an aqueous solution of *Schizophyllum commune* β-glucan, the formulation contains≥80 wt %, preferably ≥90 wt %, more preferably ≥95 wt %, more preferably ≥99 wt %, more preferably ≥99.5 wt % of the aqueous solution of *Schizophyllum commune* β-glucan, baed on total weight of the formulation.

In another preferred embodiment, in the formulation, the mass concentration of *Schizophyllum commune* β-glucan in the aqueous solution thereof is 0.0001-50 wt %, preferably 0.02-10 wt %, more preferably 0.05-5 wt % based on the total weight of the aqueous solution of *Schizophyllum commune* β-glucan.

In a preferred embodiment, the invention provides a formulation for the prevention and/or treatment of hormone-dependent dermatitis, comprising: β-glucan, 1,3-butanediol, 1,3-propanediol, polyethylene glycol 400, glycerin, hyaluronic acid, and deionized water.

In another preferred embodiment, the components of the formulation are shown in Table 1:

TABLE 1

Formulations with efficacy in the prevention and/or treatment of hormone-dependent dermatitis

| Ingredient | Amount (% or part by weight) | | |
| --- | --- | --- | --- |
| | Formulation 1 | Formulation 2 | Formulation 3 |
| β-glucan | 0.001-20 | 0.01-2 | 0.05-1 |
| 1,3-Butanediol | 0.1-5 | 0.1-5 | 0.1-5 |
| 1,3-Propanediol | 0.1-5 | 0.1-5 | 0.1-5 |
| PEG 400 | 0.1-5 | 0.1-5 | 0.1-5 |
| Glycerin | 0.1-5 | 0.1-5 | 0.1-5 |
| Hyaluronic Acid | 0.01-1 | 0.01-1 | 0.01-1 |
| Deionized water | 59-99.589 | 77-99.58 | 78-99.54 |

The "active ingredient (first active ingredient)" in the formulation or composition described in the present invention refers to the β-glucan (preferably *Schizophyllum commune* β-glucan) described in the present invention.

The "active ingredient (first active ingredient)", formulation and/or composition described in the present invention can be used for the prevention and/or treatment of hormone-dependent dermatitis.

In another preferred embodiment, the "active ingredient (first active ingredient)", formulation and/or composition are also used for the prevention and/or treatment of skin mucositis or other skin inflammatory diseases.

The "second active ingredient" refers to an active ingredient in the present invention different from the β-glucan for the treatment of hormone-dependent dermatitis, or active ingredient for treatment of skin mucositis or other skin diseases.

The "safe and effective amount" refers to an amount of the active ingredient that is sufficient to significantly improve the condition or symptoms without causing any serious side effects.

Typically, the pharmaceutical composition contains 1-2,000 mg of active ingredient/dose, more preferably 10-200 mg of active ingredient/dose. Preferably, the "one dose" is a pill or an injection.

"Pharmaceutically acceptable carrier" refers to one or more compatible solid or liquid fillers or gels suitable for human use and having sufficient purity and low enough toxicity.

"Compatibility" herein refers to the ability of each components of a composition to blend with the active ingredient of the invention and with each other that will not significantly reducing the efficacy of the active ingredient.

Some examples of pharmaceutically acceptable carriers are cellulose and its derivatives (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween®), wetting agents (such as sodium dodecyl sulfate), colorants, flavoring agents, stabilizers, antioxidants, preservatives, pyrogen-free water, and the like.

In another preferred embodiment, the β-glucan of the present invention may form a complex with a macromolecular compound or a polymer by non-bonding interaction.

In another preferred embodiment, the β-glucan of the present invention may be attached to a macromolecular compound or polymer by a bond. The macromolecular compound may be a biomacromolecule such as a polysaccharide, protein, nucleic acid, polypeptide, etc.

There is no particular limitation on the mode of administration of the active ingredient or pharmaceutical composition of the present invention, representative modes of administration include but are not limited to: topical, oral, intratumoral, rectal, parenteral (intravenous, intramuscular or subcutaneous), etc.

Solid dosage forms include capsules, tablets, pills, powders and granules.

In these solid dosage forms, the active ingredient is mixed with at least one conventional inert excipient or carrier, such as sodium citrate or dicalcium phosphate, or with one or more of the following ingredients:

(a) fillers or bulking agents, e.g., starch, lactose, sucrose, glucose, mannitol, and silicic acid;
(b) binders, e.g., hydroxymethylcellulose, alginate, gelatin, polyvinylpyrrolidone, sucrose, and gum arabic;
(c) humectants, e.g., glycerin;
(d) disintegrants, e.g., agar, calcium carbonate, potato starch or tapioca starch, alginic acid, certain complex silicates, and sodium carbonate;
(e) retarding agents, e.g., paraffin;
(F) asorption accelerators, e.g., quaternary amine compounds;
(g) wetting agents, e.g., cetanol and glycerol monosterate;
(h) adsorbent, e.g., kaolin; and/or
(i) lubricant, e.g., talc, calcium stearate, magnesium stearate, solid polyethylene glycol, sodium dodecyl sulfate, or mixtures thereof.

In capsules, tablets and pills, the dosage form may also contain a buffering agent.

The solid dosage forms may also contain coatings and shell materials, such as enteric coatings and other materials well known in the art. They may contain opacifying agents and the release of the active ingredient in such compositions may be released in a delayed manner in a portion of the digestive tract. Examples of embedding components that may be employed are polymeric substances and waxes.

The liquid dosage form comprises a pharmaceutically acceptable emulsion, solution, suspension, syrup or tincture. In addition to the active ingredients, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or mixtures thereof. In addition to these inert diluents, the composition may also contain auxiliaries such as wetting agents, emulsifiers, suspending agents, sweeteners, flavoring agents and flavors.

In addition to the active ingredient, the suspension may comprise suspending agents, such as ethoxylated isooctadecanol, polyoxyethylene sorbitol and dehydrated sorbitol esters, microcrystalline cellulose, methanolic aluminum, agar, and any mixtures thereof.

The compositions may comprise physiologically acceptable sterile aqueous or non aqueous solutions, dispersions, suspensions or emulsions, and sterile powders for redissolution into sterile injectable solutions or dispersions. Suitable aqueous and non-aqueous carriers, diluents, solvents, or excipients include water, ethanol, polyols, and suitable mixtures thereof.

When using the pharmaceutical composition, a safe and effective amount of the composition of the present invention is administered to a mammal (e.g., human) in need of treatment, wherein the dose for administration is the pharmacologically considered effective dose, which is typically 1 to 10,000 mg, preferably 10 to 2,000 mg, more preferably 20 to 1,000 mg per day for a 60 kg body weight human. Of course, the specific dose should consider the route of administration, patient's health condition and other factors, which are within the skill range of skilled doctors.

The present invention also provides a composition product, comprising:
 (1) a first pharmaceutical composition, comprising (a) a first active ingredient, and the first active ingredient is β-glucan; and (b) a pharmaceutically acceptable carrier or excipient; and
 (2) a second pharmaceutical composition, which is a therapeutic drug, different from the first active ingredient, for the treatment of hormone-dependent dermatitis, or a therapeutic drug for the treatment of skin mucositis or other skin diseases.

The compositions of the present invention may be administered alone or in combination with other therapeutic agents (e.g., formulated in one pharmaceutical composition).

The pharmaceutical composition of the present invention can also be combined with other drugs known to treat or improve similar conditions. When administered in combination, the mode of administration and dosage of the known drug may be unchanged, while the pharmaceutical composition of the present invention is administered simultaneously or subsequently. The administered in combination also includes administered the pharmaceutical composition of the present invention and one or more other known drugs at an overlapping time period. When the pharmaceutical composition of the present invention is administered in combination with one or more other drugs, the dose of the pharmaceutical composition of the present invention or the known drug may be lower than when they are administered alone.

The Main Advantages of the Invention Include:
 (a) The β-glucan of the present invention (e.g., *Schizophyllum commune* β-glucan) is very effective in preventing and/or treating hormone-dependent dermatitis.
 (b) The β-glucan of the present invention has very low side effects in the treatment of hormone-dependent dermatitis, does not disrupt the ecological balance on the skin surface flora, and does not harm the patient's skin or develop any drug resistant.
 (c) The β-glucan of the present invention not only can be used to prevent and/or treat hormone-dependent dermatitis, but also can enhance the active defense function of the skin and stimulate the cellular basal immune function while preventing excessive inflammation, having a bidirectional immunomodulatory function, which can be antibacterial, anti-inflammatory and skin repair, and can prevent and/or treat skin mucositis or other skin inflammatory diseases.
 (d) The combination of β-glucan of the present invention with other drugs for the treatment of hormone-dependent dermatitis can further enhance the preventive and/or therapeutic effect, having synergistic effect.
 (e) The β-glucan (preferably, *Schizophyllum commune* β-glucan) of the present invention is a natural biopolysaccharide, is fully soluble or naturally soluble, and has not been changed or modified in any chemical and/or physical way.
 (f) The β-glucan of the present invention retains the three-dimensional conformation of triple helix intactly and has better preventive and/or therapeutic activity against hormone-dependent dermatitis.
 (g) The β-glucan of the present invention has excellent stability and can coexist with most substances while maintaining its activity, and thus has a wide range of application areas and can be used in combination with other hormone-dependent dermatitis treatment drugs or skin care products to improve skin quality while preventing and treating hormone-dependent dermatitis.

The present invention will be further explained below in conjunction with specific embodiments. It should be understood that these embodiments are only used to illustrate the present invention and not to limit the scope of the present invention. The experimental methods that do not indicate specific conditions in the following examples usually follow the conventional conditions, such as those described in Sambrook et al., Molecular Cloning: A Laboratory Manual (New York: Cold Spring Harbor Laboratory Press, 1989), or the conditions suggested by the manufacturer. Unless otherwise specified, percentages and parts are percentages by weight and parts by weight.

Unless otherwise specified, the experimental methods used in the following examples are conventional methods.

Unless otherwise specified, the materials, reagents, equipment, etc. used in the following examples are commercially available.

Example 1. Acquisition and Determination of β-Glucan

The example only takes the Acquisition of β-glucan by fermenting *Schizophyllum commune* as an example, but it is not limited thereto.

I. Acquisition of Fermentation Broth of *Schizophyllum commune* Strain

The fermentation broth in the following Examples was obtained from *Schizophyllum commune* strain (*Schizophyllum commune* Fr-1003, catalog: ATCC®38548™, purchased from the American Type Collection Center [ATCC]) by fermenting, as follows:
 1. activation of *Schizophyllum commune* strain: *Schizophyllum commune* strain was inoculated onto a plate medium made of potato powder 200 g/L, glucose 30 g/L, sodium chloride 10 g/L and agar 20 g/L, incubated at 25° C. in a constant temperature incubator for 7 days to obtain plate mycelium;

2. activation of seed: a liquid medium made of potato starch 100 g/L, glucose 40 g/L, yeast extract 2 g/L, yeast extract powder 2 g/L and water was charged into a shake flask with a ⅓ liquid volume, then the plate mycelium obtained from step 1 was inoculated into the shake flask, and incubated in a constant temperature shaker at 25° C. for 7 days with 160 rpm shaking, to obtained a seed solution;

3. fermentation and cultivation: a fermentation medium made of glucose 50 g/L, sucrose 50 g/L, soybean powder (Shandong Zhaoyuan Wenzhi Food Co., Ltd.) 5 g/L, yeast extract powder 2 g/L, potassium dihydrogen phosphate 0.5 g/L, magnesium sulfate heptahydrate 0.5 g/L, ammonium sulfate 0.5 g/L, potassium nitrate 6 g/L and water was added into fermenter and sterilized at 121° C. for 15 minutes, then the seed solution obtained from step 2 was inoculated into the above fermenter, and fermented under 4 Lpm aeration at 25° C. constant temperature with 300 rpm stirring for 8 days, to obtain the fermentation broth of *Schizophyllum commune*.

II. Isolation and Purification of β-Glucan and Preparation of β-Glucan Solution (1) The fermentation broth of *Schizophyllum commune* obtained from the above part I was mixed with 4 times the volume of distilled water and digested at 60° C. for 8 h to obtain the digestion solution.

(2) The digestion solution obtained from step (1) was centrifuged at 4,000 rpm for 5 min, the supernatant was taken and filtered through 300 mesh filter cloth under negative pressure to obtain the filtrated clear solution, which is digestion clear solution;

(3) The filtrated digestion clear solution obtained from step (2) was heated to 50° C., and a 200-mesh wooden activated carbon and a 8-16-mesh coconut shell activated carbon were added thereto, wherein the volume of each activated carbon added is 1% of the volume of the digestion clear solution, stirred for 4 h at 50° C. and 350 rpm, cooled and ready for use, to obtain a digestion clear solution mixed with activated carbon; then the digestion clear solution mixed with activated carbon was successively filtered though 300 mesh filter cloth and SCP-321 # filter plate (pore size about 1.5 μm) under negative pressure to obtain the filtrate for use.

(4) Solarbio lipase (L8070, enzyme activity 100-400 U/mg) was dissolved in physiological phosphate buffer, the solution of Solarbio lipase was added into the filtrate prepared in step (3) at an enzyme dosage of 10 U/mL, stirred well and then enzymatically digested at 40° C. for 2 h; then Solarbio neutral protease (Z8030, enzyme activity>60 U/mg) was dissolved in physiological phosphate buffer, the solution of Solarbio neutral protease was added into the above enzymatic hydrolysate at an enzyme dosage of 60 U/mL, stirred well and then enzymatically digested at 40° C. for 2 h. After the enzymatic digestion was completed, the mixture was heated in a water bath at 90° C. for 30 min to inactivate the enzyme, and then filtered though SCP-321 # filter plate (pore size about 1.5 μm) under negative pressure to obtain the filtrated clear liquid for use.

(5) The filtrated clear liquid of step (4) was mixed with 95% edible ethanol (volume ratio of 1:3) quickly and stirred until obtaining precipitates; then the precipitates were redissolved to the original volume, mixed with 95% edible ethanol (volume ratio of 1:3) quickly and stirred until obtaining precipitates.

(6) The precipitates obtained from step (5) were placed in a tray with holes and dried in an electric oven at 40° C. until the weight constant, to obtain a dried product.

(7) The dried product of β-glucan obtained from step (6) was crushed, 5 g of the crushed product was weighed and dissolved into 1,000 mL of ultrapure water, stirred at 600 rpm for 2 h until the β-glucan is fully dissolved to obtain a β-glucan solution; the β-glucan solution was filtered though a 5-μm filter membrane under negative pressure, and an appropriate amount of preservative for cosmetics was added to obtain a β-glucan solution with a concentration of 0.5% having high-viscosity and high-transmittance.

The β-glucan solution with a mass concentration of 0.5% can reach 90% light transmittance at 600 nm (detected by spectrophotometer), and the viscosity at 40° C. can reach more than 600 mPa·s.

III. Identification and Detection of the β-Glucan

1. Identification of β-Glucan by Infrared Spectroscopy

The above 0.5% β-glucan solution was identified, specifically by using infrared spectroscopy according to Method C in Appendix IV, Part II of the Pharmacopoeia of the People's Republic of China (2010 Edition). The sample dried at 105° C. was scanned at full wavelength using a Fourier transform infrared spectrometer. Result: 0.5% solution obtained in step (7) of the above part II of Example 1 is a β-glucan solution.

Compared with the infrared spectrogram of yeast β-glucan in the yeast β-glucan industry standard QBT 4572-2013, the positions of functional groups thereof are basically matched. As shown in FIG. 1, the positions of main functional groups are:

1) A stronger and broader absorption peak near 3301 cm$^{-1}$ (O—H bond stretching vibration absorption peaks of saccharides);
2) A weaker absorption peak near 2921 cm$^{-1}$ (C—H bond stretching vibration absorption peak of saccharides);
3) Weaker absorption peaks near 886 cm$^{-1}$ (β-configuration characteristic vibration absorption peaks of saccharides);
4) Stronger absorption peaks near 1076 cm$^{-1}$ (C—OH, C—O—C stretching vibration absorption peaks of saccharides)

The results of Fourier transform infrared spectroscopy showed that the product obtained in this example is β-glucan.

2. β-Glucan Content Detection

The β-glucan quantification of the dried product obtained from step (6) in the above part II of Example 1 was performed, specifically according to the method for determining yeast β-glucan content in the yeast β-glucan industry standard QBT 4572-2013, the sample of obtained dried product of β-glucan was grinded to a diameter of about 1.0 mm. The result shows that the β-glucan content in the product was 99.23%.

3. Hormone Assay of β-Glucan Solution 48 hormone determinations were performed on the above 0.5% β-glucan solution, specifically performed according to First method, High pressure liquid chromatography –diode array detector method, in 2.4 7 components including estriol, Chapter 4, "Cosmetics Safety Technical Specifications" (2015 Edition), and Liquid chromatography/tandem mass spectrometry and thin layer chromatography in Determination of forty-one glucocorticoids in cosmetics, GB/T24800.2-2009. As a result, the above hormones were not detected in the 0.5% β-glucan solution obtained from step (7) of the above part II of Example (see Table 2).

TABLE 2

48 hormone determinations

| Number | Category | Hormone component | Result(μg/g) | Detection limit(μg/g) | Method |
|---|---|---|---|---|---|
| 1 | Gonadal | Estriol | Not Detected | 40 | "Cosmetics Safety Technical |
| 2 | hormone | Estrone | Not Detected | 80 | Specifications" (2015 Edition) |
| 3 | | Stilboestrol | Not Detected | 20 | Chapter 4, 2.4 7 components |
| 4 | | Estradiol | Not Detected | 40 | including estriol, First method, |
| 5 | | Testosterone | Not Detected | 4 | High pressure liquid |
| 6 | | Methyltestosterone | Not Detected | 4 | chromatography-diode |
| 7 | | Progesterone | Not Detected | 6 | array detector method |
| 8 | Glucocorticoid | Prednisone | Not Detected | 0.03 | GB/T24800.2-2009 |
| 9 | | Cortisone | Not Detected | 0.03 | GB/T24800.2-2009 |
| 10 | | Prednisolone | Not Detected | 0.03 | GB/T24800.2-2009 |
| 11 | | Hydrocortisone | Not Detected | 0.03 | GB/T24800.2-2009 |
| 12 | | Methylprednisolone | Not Detected | 0.03 | GB/T24800.2-2009 |
| 13 | | fluorometholone | Not Detected | 0.03 | GB/T24800.2-2009 |
| 14 | | Betamethasone | Not Detected | 0.03 | GB/T24800.2-2009 |
| 15 | | Dexamethasone | Not Detected | 0.03 | GB/T24800.2-2009 |
| 16 | | Triamcinolone | Not Detected | 0.03 | GB/T24800.2-2009 |
| 17 | | Prednisone acetate | Not Detected | 0.03 | GB/T24800.2-2009 |
| 18 | | Cortisone acetate | Not Detected | 0.03 | GB/T24800.2-2009 |
| 19 | | Prednisolone acetate | Not Detected | 0.03 | GB/T24800.2-2009 |
| 20 | | Hydrocortisone acetate | Not Detected | 0.03 | GB/T24800.2-2009 |
| 21 | | Beclomethasone | Not Detected | 0.03 | GB/T24800.2-2009 |
| 22 | | Flumethasone | Not Detected | 0.03 | GB/T24800.2-2009 |
| 23 | | Methylprednisolone acetate | Not Detected | 0.03 | GB/T24800.2-2009 |
| 24 | | Fluorometholone Acetate | Not Detected | 0.03 | GB/T24800.2-2009 |
| 25 | | fludrocortisone acetate | Not Detected | 0.03 | GB/T24800.2-2009 |
| 26 | | Budesonide | Not Detected | 0.03 | GB/T24800.2-2009 |
| 27 | | Hydrocortisone butyrate | Not Detected | 0.03 | GB/T24800.2-2009 |
| 28 | | Triamcinolone acetonide | Not Detected | 0.03 | GB/T24800.2-2009 |
| 29 | | Dexamethasone Acetate | Not Detected | 0.03 | GB/T24800.2-2009 |
| 30 | | Betamethasone acetate | Not Detected | 0.03 | GB/T24800.2-2009 |
| 31 | | Flurandrenolide | Not Detected | 0.03 | GB/T24800.2-2009 |
| 32 | | Deflazacort | Not Detected | 0.03 | GB/T24800.2-2009 |
| 33 | | Hydrocortisone valerate | Not Detected | 0.03 | GB/T24800.2-2009 |
| 34 | | Halcinonide | Not Detected | 0.03 | GB/T24800.2-2009 |
| 35 | | Clobetasol propionate | Not Detected | 0.03 | GB/T24800.2-2009 |
| 36 | | Betamethasone valerate | Not Detected | 0.03 | GB/T24800.2-2009 |
| 37 | | Triamcinolone acetonide acetate | Not Detected | 0.03 | GB/T24800.2-2009 |
| 38 | | Clobetasone Butyrate | Not Detected | 0.03 | GB/T24800.2-2009 |
| 39 | | Prednicarbate | Not Detected | 0.03 | GB/T24800.2-2009 |
| 40 | | Diflorasone diacetate | Not Detected | 0.03 | GB/T24800.2-2009 |
| 41 | | Fluocinonide | Not Detected | 0.03 | GB/T24800.2-2009 |
| 42 | | Amcinonide | Not Detected | 0.03 | GB/T24800.2-2009 |
| 43 | | Betamethasone dipropionate | Not Detected | 0.03 | GB/T24800.2-2009 |
| 44 | | Beclomethasone dipropionate | Not Detected | 0.03 | GB/T24800.2-2009 |
| 45 | | Mometasone furoate | Not Detected | 0.03 | GB/T24800.2-2009 |
| 46 | | Alclometasone Dipropionate | Not Detected | 0.03 | GB/T24800.2-2009 |
| 47 | | Fluticasone propionate | Not Detected | 0.03 | GB/T24800.2-2009 |
| 48 | | Triamcinolone diacetate | Not Detected | 0.03 | GB/T24800.2-2009 |

4. Viscosity Determination of β-Glucan Solutions

According to the method of step (7) in the part II of Example 1, β-glucan aqueous solutions of 0.3%, 0.5%, 0.8% and 1.0% (mass to volume ratio) were prepared, and the kinetic viscosities were tested at 25° C., respectively. The results showed in Table 3, the viscosity of each sample increases with the increase of β-glucan content, which are 472, 740, 2150 and 3100 mPa·s, respectively.

Commercially available dispersible (insoluble in water) yeast β-glucan granules (purchased from Wellmune) was taken and accurately weighed 2 g, mixed with deionized water and fixed to 200 mL to obtain a yeast β-glucan aqueous solution with a mass to volume ratio of 1.0%, and the kinetic viscosity was tested at 25° C. The kinetic viscosity of the 1.0% yeast β-glucan suspension was 0 mPa·s (see Table 3).

Commercially available soluble yeast β-glucan powder (purchased from Wellmune) was taken and weighed 2 g, dissolved by adding deionized water, and fixed to 200 mL to obtain a yeast β-glucan aqueous solution with a mass to volume ratio of 1.0%, and the kinetic viscosity was tested at 25° C. The result shows that the kinetic viscosity of the 1.0% yeast β-glucan aqueous solution was 0 mPa·s (see Table 3).

Determination method for the above kinetic viscosity was as follows:
(1) 200 mL sample of the above solution was placed in a 250 mL beaker;
(2) the beaker containing the above solution/mixture sample is placed in a water bath and maintained at 25° C. for 1 h.
(3) the kinetic viscosity at 25° C. of each sample was tested by using a rotational viscometer.

5. Detection of Light Transmittance of β-Glucan Solution

According to the method of step (7) in the part II of Example 1, β-glucan aqueous solutions of 0.3%, 0.5%, 0.8% and 1.0% (mass to volume ratio) were prepared, and the light transmittance of the solutions were measured at 600 nm. The results show in Table 3, and the light transmittance of each sample was 96.5%, 93.1%, 87.5% and 81.1%, respectively.

Commercially available 1.0% oat β-glucan solution (purchased from Symrise) was taken and the light transmittance thereof was measured at 600 nm, as a result the light transmittance is 59.7% (see Table 3).

Commercially available dispersible yeast β-glucan granules were taken and weighed 2 g, mixed with deionized water and fixed to 200 mL to obtain a yeast β-glucan suspension with a mass to volume ratio of 1.0%, and the light transmittance of the suspension was measured at 600 nm, as a result the light transmittance is only 1.3% (see Table 3).

Detection method of the above light transmittance was as follows:
(1) 10 mL of the above solution sample was placed in a centrifuge tube.
(2) centrifugating at a low speed of 1000 rpm for 1 min to remove air bubbles (both yeast β-glucan solutions/suspensions were free of air bubbles and were not treated by centrifugation).
(3) Then 3 mL of the sample was carefully placed into a 1 cm glass cuvette, avoiding air bubbles.
(4) The light transmittance of sample was measured at 600 nm by a spectrophotometer with deionized water as a blank reference (counting the light transmittance of deionized water as 100%).

6. Stability Determination of β-Glucan Solution

Figure 2:
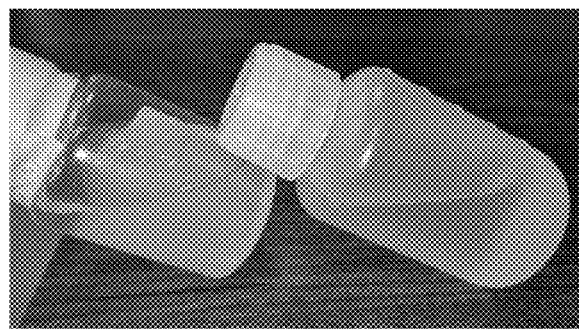
FIG. 2 shows a comparison of the stability of β-glucan, the left one is a commercially available 1.0% oat β-glucan solution, and the right one is 1.0% Schizophyllum commune β-glucan prepared by the present invention.

According to the method of step (7) in the part II of Example 1, β-glucan aqueous solutions of 0.5%, 0.8% and 1.0% (mass to volume ratio) were prepared, and after adding preservatives, the solutions were placed at room temperature (no protection from light) for 24 months, the stability of the solutions was to observed and the kinetic viscosity and light transmittance of the solutions were detected. As a result, the state of the above three solutions are very stable, and their viscosity and light transmittance do not change much, wherein the light transmittance even increased (see FIG. 2 and Table 3).

Commercially available 1.0% oat β-glucan solution was placed at room temperature (no protection from light) for 24 months, the stability of the solution was observed and the kinetic viscosity and light transmittance of the solution were detected. As a result, the state of the 1.0% oat β-glucan solution is very unstable, with solid precipitated after 3 months at room temperature, resulting in undetectable viscosity and transmittance (see FIG. 2 and Table 3).

TABLE 3 kinetic viscosity data of various β-glucan solutions

| Solution Number | Source of β-glucan | β-glucan Concentration (%) | Kinetic viscosity (mPa·s, 25° C.) Start | Kinetic viscosity (mPa·s, 25° C.) 24 months later | Light transmittance (%) Start | Light transmittance (%) 24 months later | Stability |
|---|---|---|---|---|---|---|---|
| 1 | Schizophyllum commune (SPG) | 0.3 | 472 | — | 96.5 | — | — |
| 2 | | 0.5 | 740 | 740 | 93.1 | 98.2 | Stable solution |
| 3 | | 0.8 | 2150 | 1860 | 87.5 | 90.9 | Stable solution |
| 4 | | 1.0 | 3100 | 3080 | 81.1 | 81.8 | Stable solution |
| 5 | Oats | 1.0 | — | Undetectable | 59.7 | Undetectable | precipitated |
| 6 | Yeast[a] | 1.0 | 0 | | 1.3 | | — |
| 7 | Yeast[b] | 1.0 | 0 | | 68.4 | | — |

Note:
[a] is commercially available dispersible yeast β-glucan granules (insoluble in water),
[b] is commercially available soluble yeast β-glucan powder.

Commercially available soluble yeast β-glucan powder was taken and weighed 2 g, dissolved by adding deionized water, and fixed to 200 mL to obtain a yeast β-glucan solution with a mass to volume ratio of 1.0%, and the light transmittance of the solution was measured at 600 nm, as a result the light transmittance is 68.4% (see Table 3).

Example 2: Cream for Treatment of Hormone-Dependent Dermatitis with β-Glucan as Effective Ingredient The cream for the treatment of hormone-dependent dermatitis was formulated according to the formulation in Table 4.

TABLE 4

Formulation of cream for treatment of hormone-dependent dermatitis with β-glucan as an effective ingredient

| Ingredient | Formulation 1 | Formulation 2 | Formulation 3 | Formulation 4 | Formulation 5 | Formulation 6 | Formulation 7 | Formulation 8 |
|---|---|---|---|---|---|---|---|---|
| *Schizophyllum commune* β-glucan | 0.2% | 0.1% | 0.05% | 0.02% | — | — | — | — |
| Soluble yeast β-glucan | — | — | — | — | 0.2% | 0.1% | 0.05% | 0.02% |
| GTCC | 5% | 5% | 5% | 5% | 5% | 5% | 5% | 5% |
| Polyglyceryl ether-26 | 3% | 3% | 3% | 3% | 3% | 3% | 3% | 3% |
| AVC | 0.8% | 0.8% | 0.8% | 0.8% | 0.8% | 0.8% | 0.8% | 0.8% |
| PEG-60 | 0.5% | 0.5% | 0.5% | 0.5% | 0.5% | 0.5% | 0.5% | 0.5% |
| Water | to 100% | to 100% | to 100% | to 100% | to 100% | to 100% | to 100% | to 100% |

The samples obtained from Formulation 1 and Formulation 5 were respectively mixed with commercial pimecrolimus cream (containing 1% pimecrolimus) in ratio of 1:1 to prepare combination medicines containing 0.1% β-glucan and 0.5% pimecrolimus.

Figure 3:
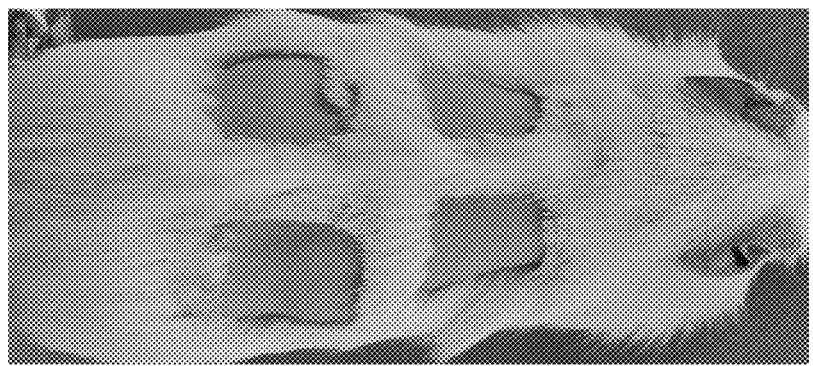
FIG. 3 shows the hair removed dorsal area of guinea pig used for the experiment in Example 3.

Example 3: Therapeutic Effect of β-Glucan on Hormone-Dependent Dermatitis 1. 7 to 9 Week old female guinea pigs with body weight of about 300 g were used and feeded for one week for adaptation to the new environment with free intake of feed and water.
2. After anesthesia by abdominal injection of chloral hydrate, the dorsum was debrided to expose the dorsal skin (FIG. 3).
3. A 0.05% clobetasol propionate solution was evenly applied externally to the exposed dorsal skin twice a day via cotton swab, the application was stopped after 15 consecutive days, and the skin was observed daily until dermatitis such as papules appeared on the skin to establish a hormone-dependent dermatitis model.
4. According to the grouping in Table 5, the positive drug (commercial pimecrolimus cream) and 10 creams prepared in Example 2 (different sources of β-glucan, and β-glucan combined with positive drugs) were evenly applied to the hormone-dependent dermatitis site on the dorsum of guinea pigs, twice a day with 0.1 g/9 cm$^2$ for each time.
5. Photographs were taken everyday to observe the treatment effect on hormone-dependent dermatitis.

Figure 4:
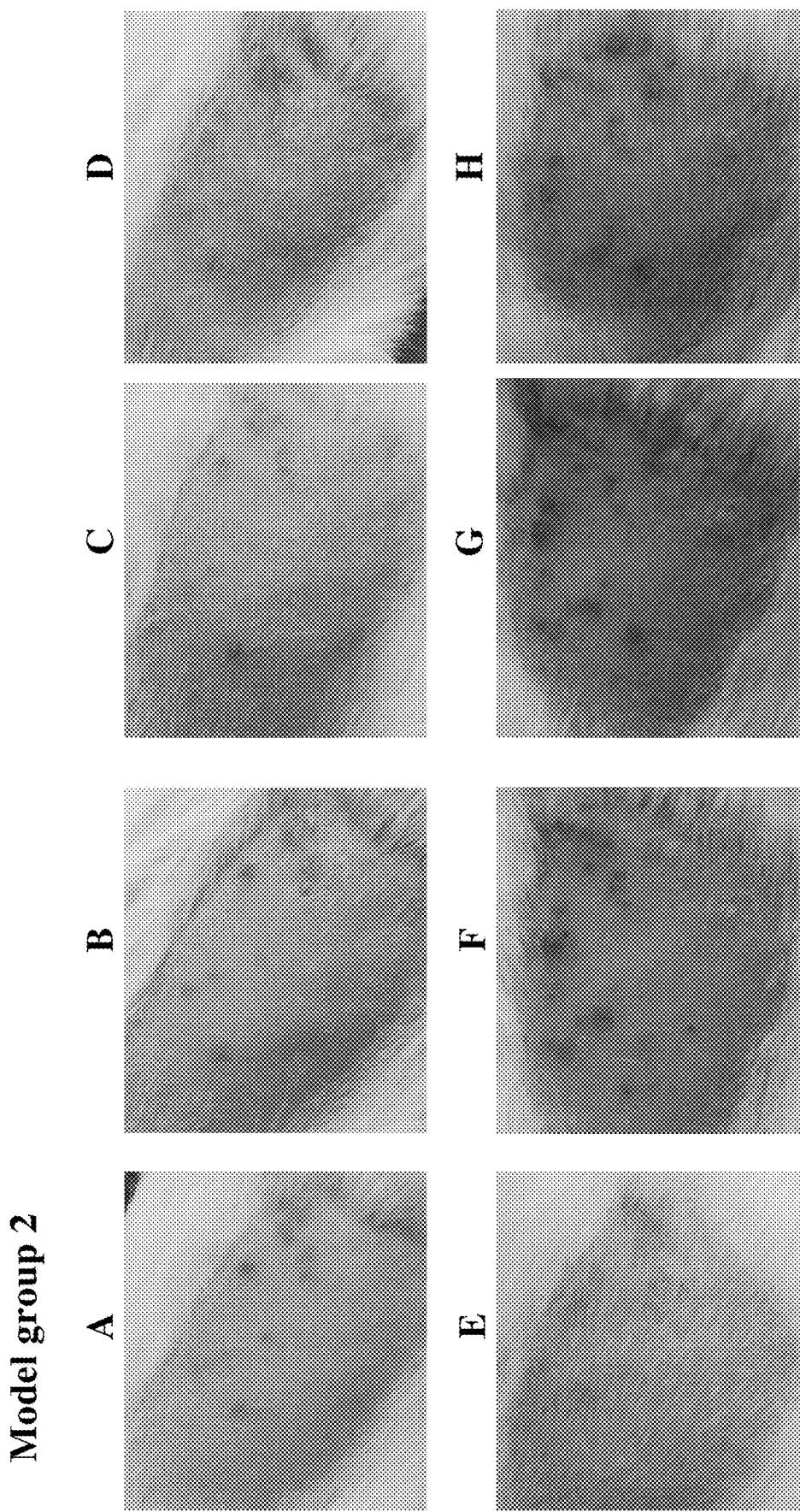
FIG. 4 shows the changes of skin inflammation in the guinea pigs of the model group in Example 3 from the 7th day after stopping applying clobetasol propionate solution. A, B, C, D, E, F, G, and H are the 7th, 8th, 9th, 10th, 11th, 12th, 13th, and 14th day after stopping hormone application, respectively.

It was found that red papules appeared in the area applied with clobetasol propionate from the 7th day after stopping the application of hormone, and the papules became more and more severe over time (FIG. 4, the 9th, 10th, 11th and 14th day of the stop of application, some of the red papules were covered by hair due to the growth of dorsal hair), and the hormone-dependent dermatitis model was successfully established.

After treatment in groups according to Table 5, it was found that all groups of drugs and combinations have therapeutic effects on hormone-dependent dermatitis (FIGS. 5-15).

(1) The positive drug group (FIGS. 5A and B) shows the fastest effect, with basically complete improvement by the next day.

(2) Although the red papules in the positive drug group fastest disappeared, careful observation revealed that the skin in this group started to become overall redness on the 4th day, and with continuously applying the positive drug, the papules occurred again on the skins in this group instead, and the skins started to become inflamed and edematous (FIG. 5D-H). The results indicate that the positive drug, although fast-acting, has greater side effects on the skin; the severity of symptoms increased substantially when the dermatitis recurred than first occurred.

(3) Both kinds of β-glucan also have therapeutic effects on hormone-dependent dermatitis. Different concentrations of *Schizophyllum commune* β-glucan (FIGS. 6-9,

TABLE 5

Experimental grouping of the treatment/relapse prevention effects of β-glucan on hormone-dependent dermatitis

| Number | Groups | | Note |
|---|---|---|---|
| 1 | model group | — | Distilled water |
| 2 | Treatment group | Positive drug group | Pimecrolimus cream (containing 1% pimecrolimus) |
| 3 | | *Schizophyllum commune* β-glucan | 0.2%, 0.1%, 0.05%, 0.02% *Schizophyllum commune* β-glucan |
| 4 | | Soluble yeast β-glucan group | 0.2%, 0.1%, 0.05%, 0.02% soluble yeast β-glucan |
| 5 | | *Schizophyllum commune* β-glucan combined with positive drug group | 0.1% *Schizophyllum commune* β-glucan + 0.5% pimecrolimus |
| 6 | | Soluble yeast β-glucan combined with positive drug group | 0.1% soluble yeast β-glucan + 0.5% pimecrolimus |

A-D in each figure) and soluble yeast β-glucan (FIGS. 10-13, A-D in each figure) showed various degrees of improvement on the second day of treatment. By the fourth day, the red papules in most of the *Schizophyllum commune* β-glucan-treated groups basically subsided, except for the 0.02% *Schizophyllum commune* β-glucan group injured during depilation, while only the 0.2% soluble yeast β-glucan group (FIG. 10) has a more obvious effect, and the red papules did not disappear completely in the remaining concentrations. It can be seen that the therapeutic effect of *Schizophyllum commune* β-glucan on hormone-dependent dermatitis is better than that of soluble yeast β-glucan.

(4) In the *Schizophyllum commune* β-glucan (FIGS. 6-9, A-D in each figure) groups and soluble yeast β-glucan (FIGS. 10-13, A-D in each figure) groups, the skins gradually become clear and smooth and free of edema and inflammation in the first four days of continuous treatment. From the fifth day, hormone-dependent dermatitis relapsed in both groups (FIGS. 6-9, E and F in each figure, and FIGS. 10-13, E and F in each figure), and papules appeared again, but severity thereof is substantially lower than the first occurrence (FIGS. 6-9, A in each figure, and FIGS. 10-13, A in each figure). The papules then improved again with the continuation of treatment. In the groups treated with 0.05%, 0.1% and 0.2% *Schizophyllum commune* β-glucan, there was no recurrence, and in the group treated with 0.02% *Schizophyllum commune* β-glucan and various concentrations of soluble yeast β-glucan, it was cured after 1-2 recurrences.

Figure 5:
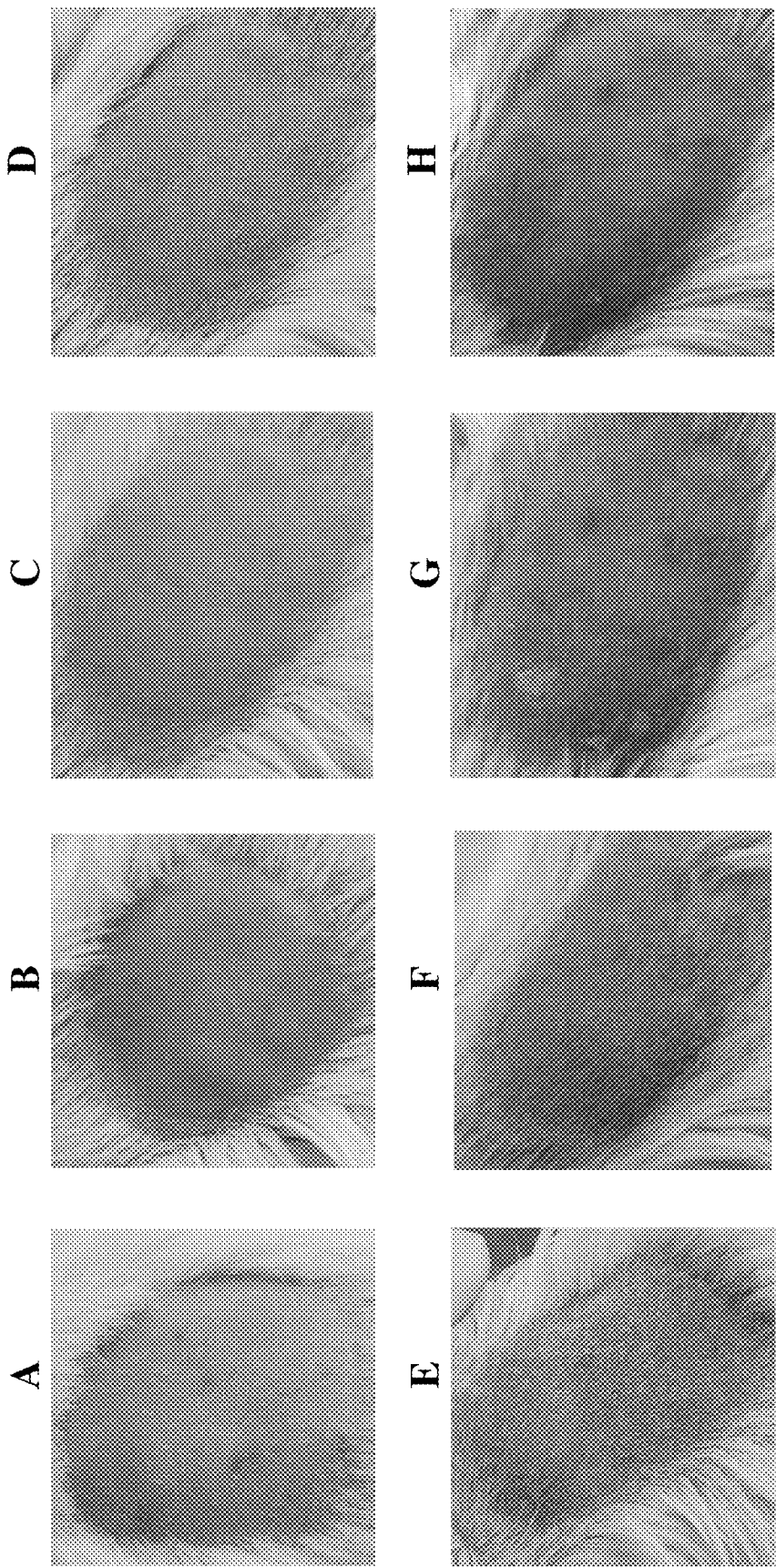
FIG. 5 shows the changes of skin inflammation in guinea pigs of the positive drug treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 6:
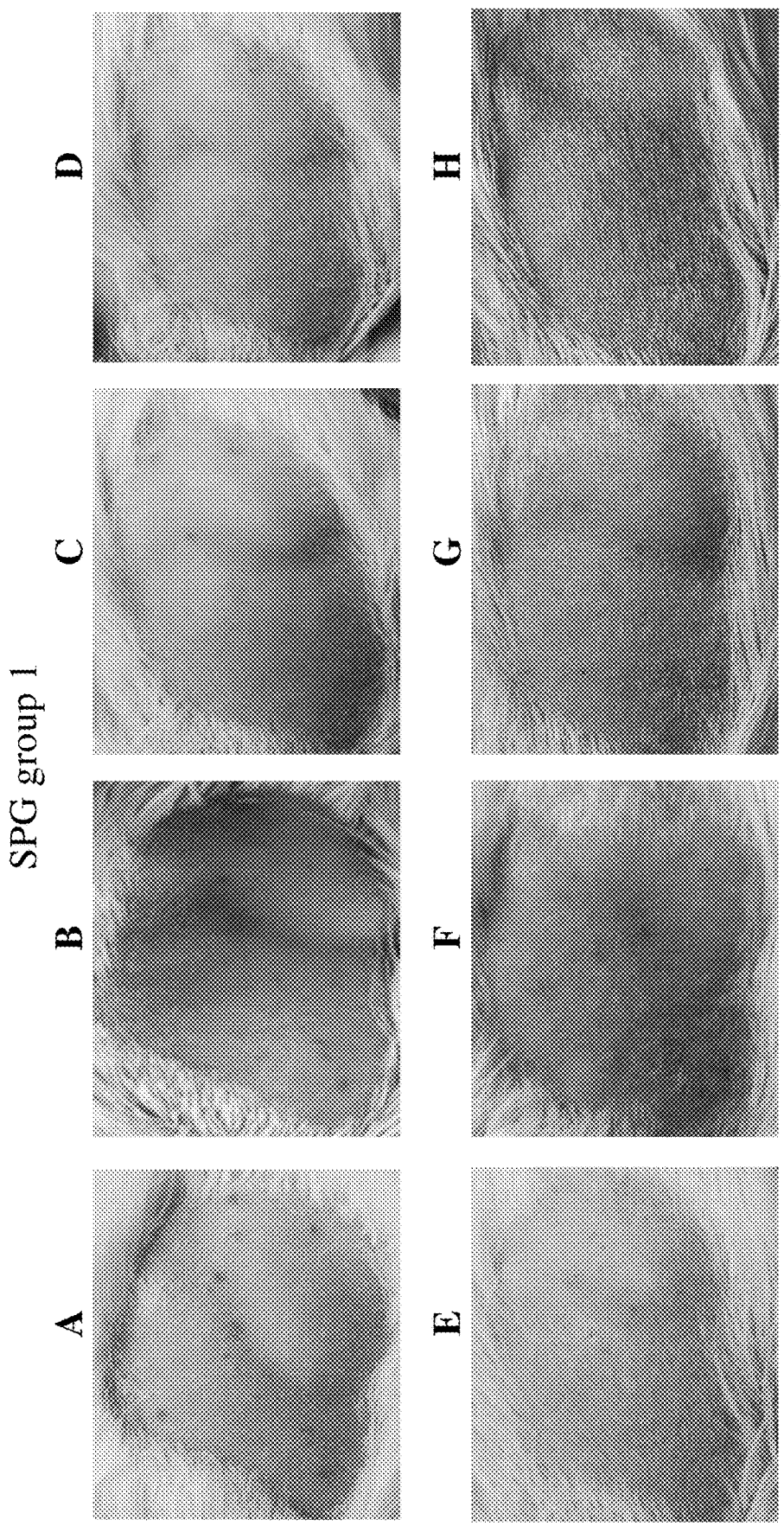
FIG. 6 shows the changes of skin inflammation in guinea pigs of the 0.2% Schizophyllum commune β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 7:
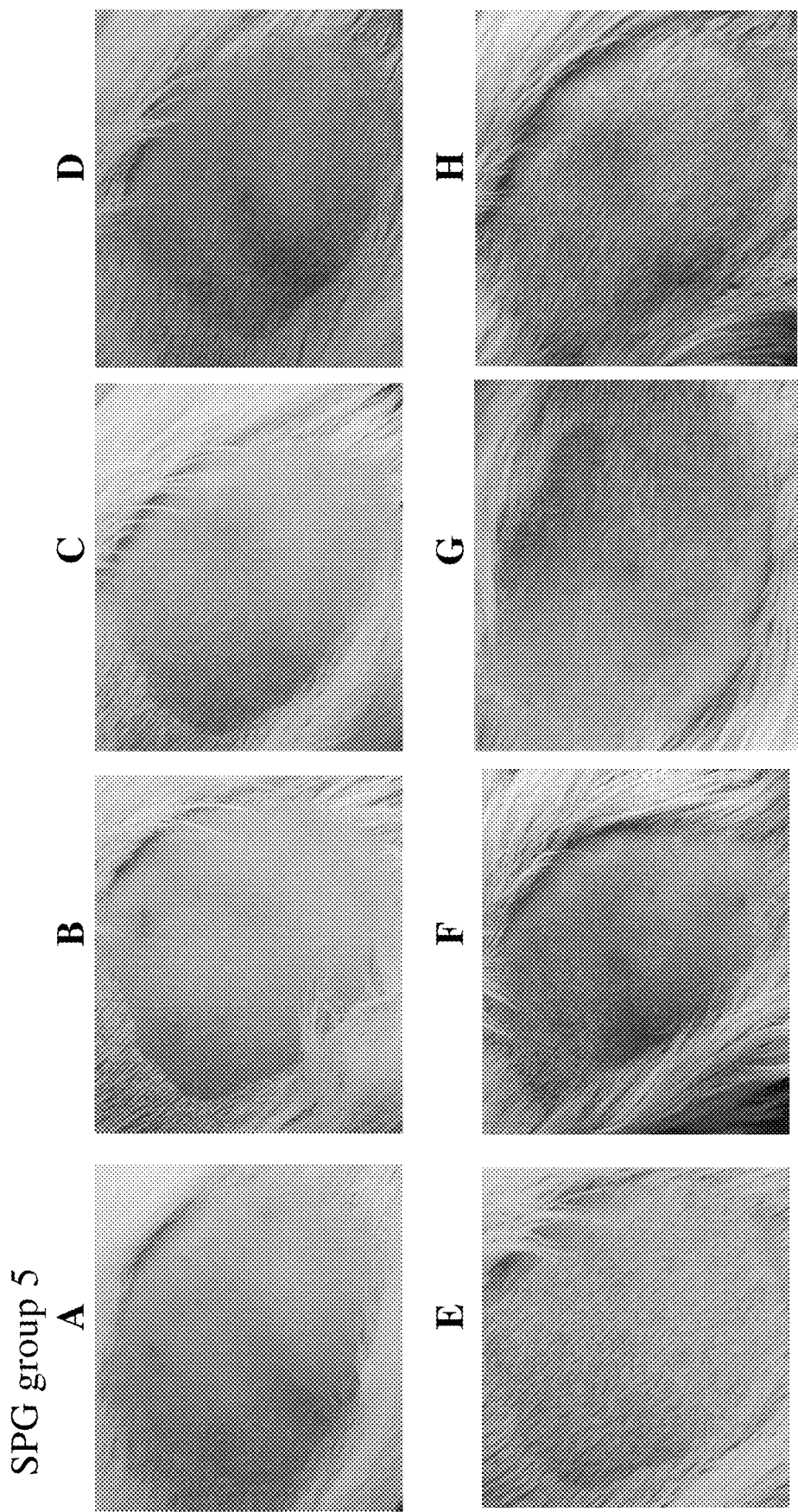
FIG. 7 shows the changes of skin inflammation in guinea pigs of the 0.1% Schizophyllum commune β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 8:
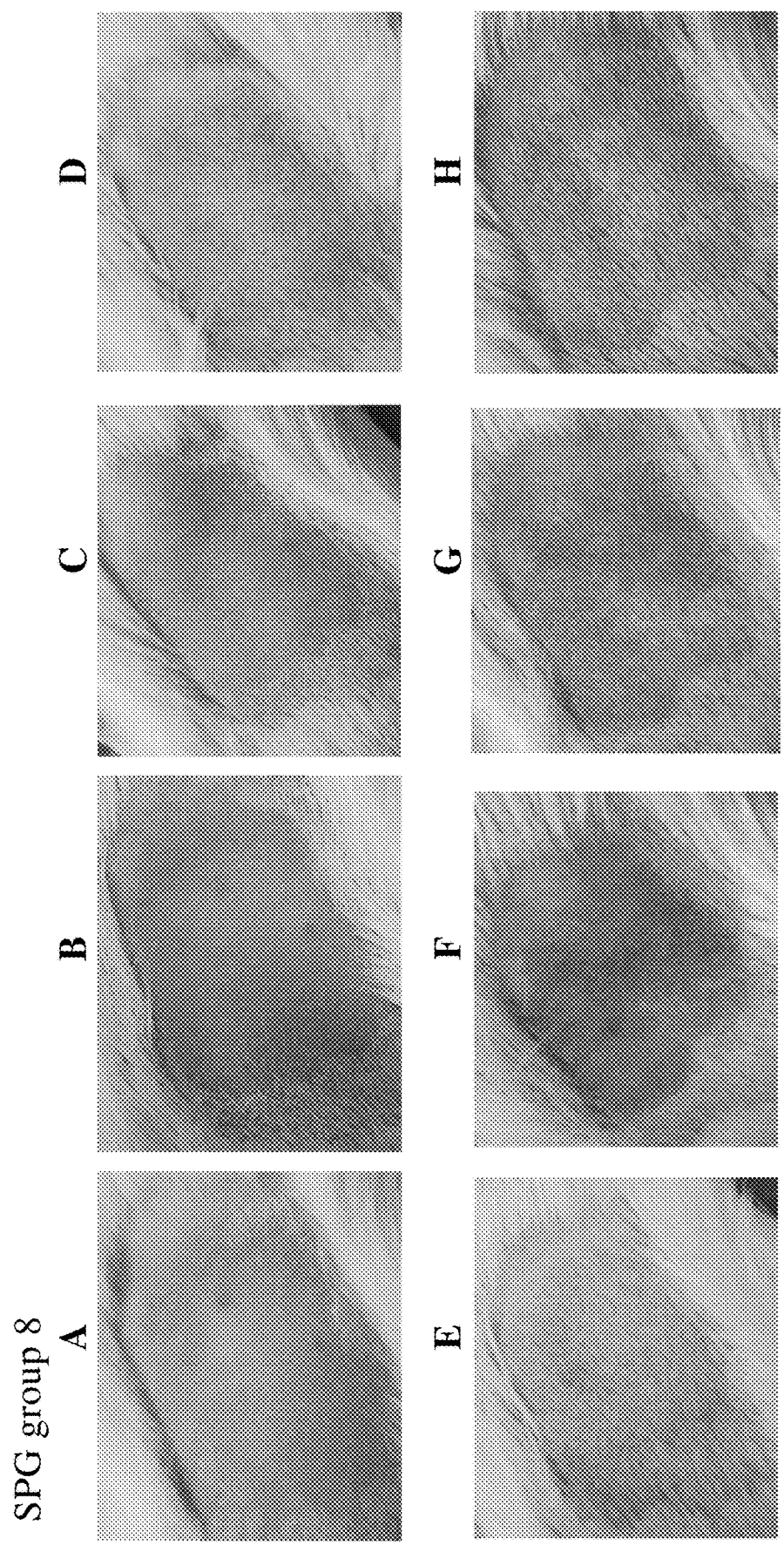
FIG. 8 shows the changes of skin inflammation in guinea pigs of the 0.05% Schizophyllum commune β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 9:
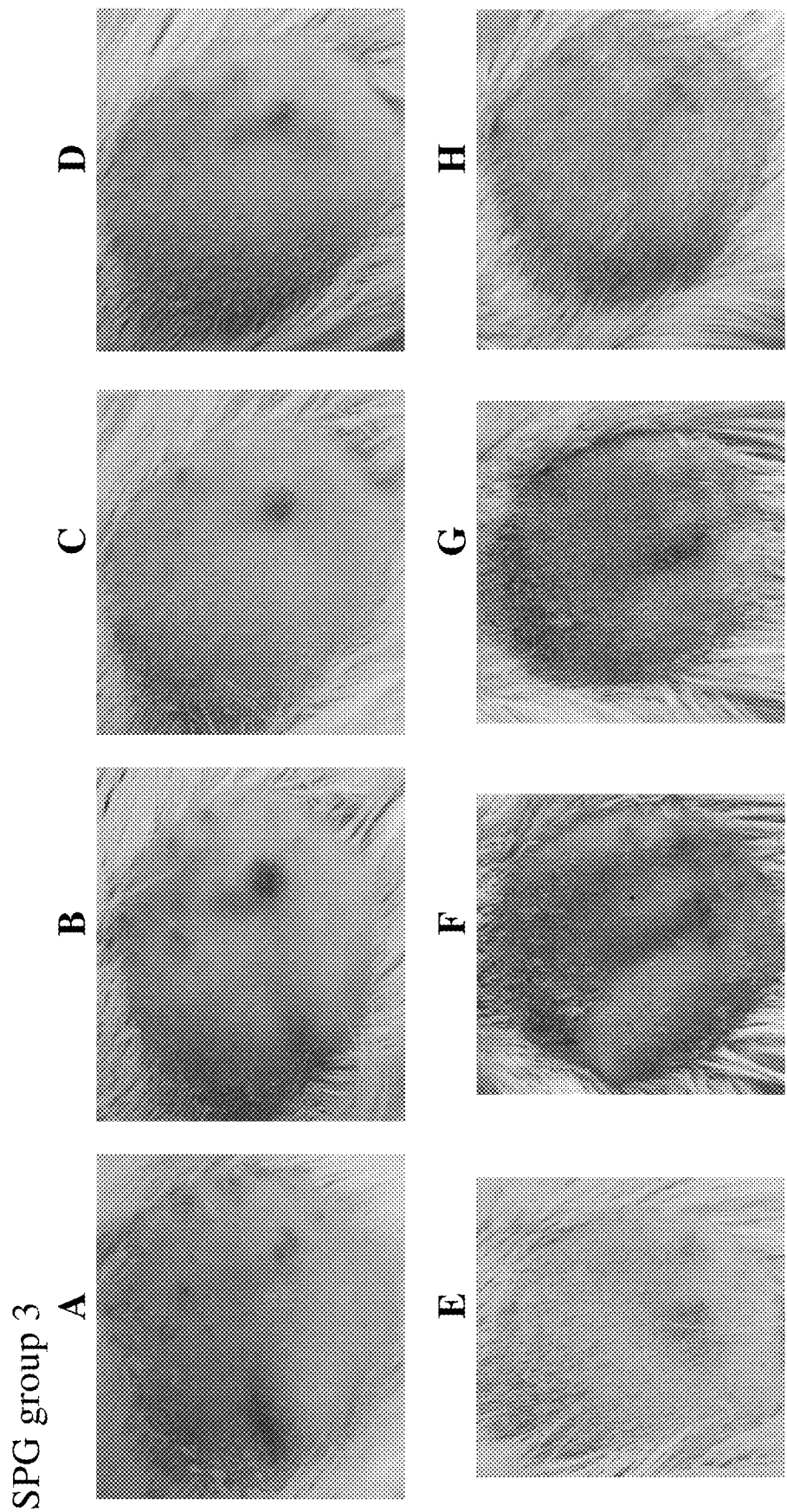
FIG. 9 shows the changes of skin inflammation in guinea pigs of the 0.02% Schizophyllum commune β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 10:
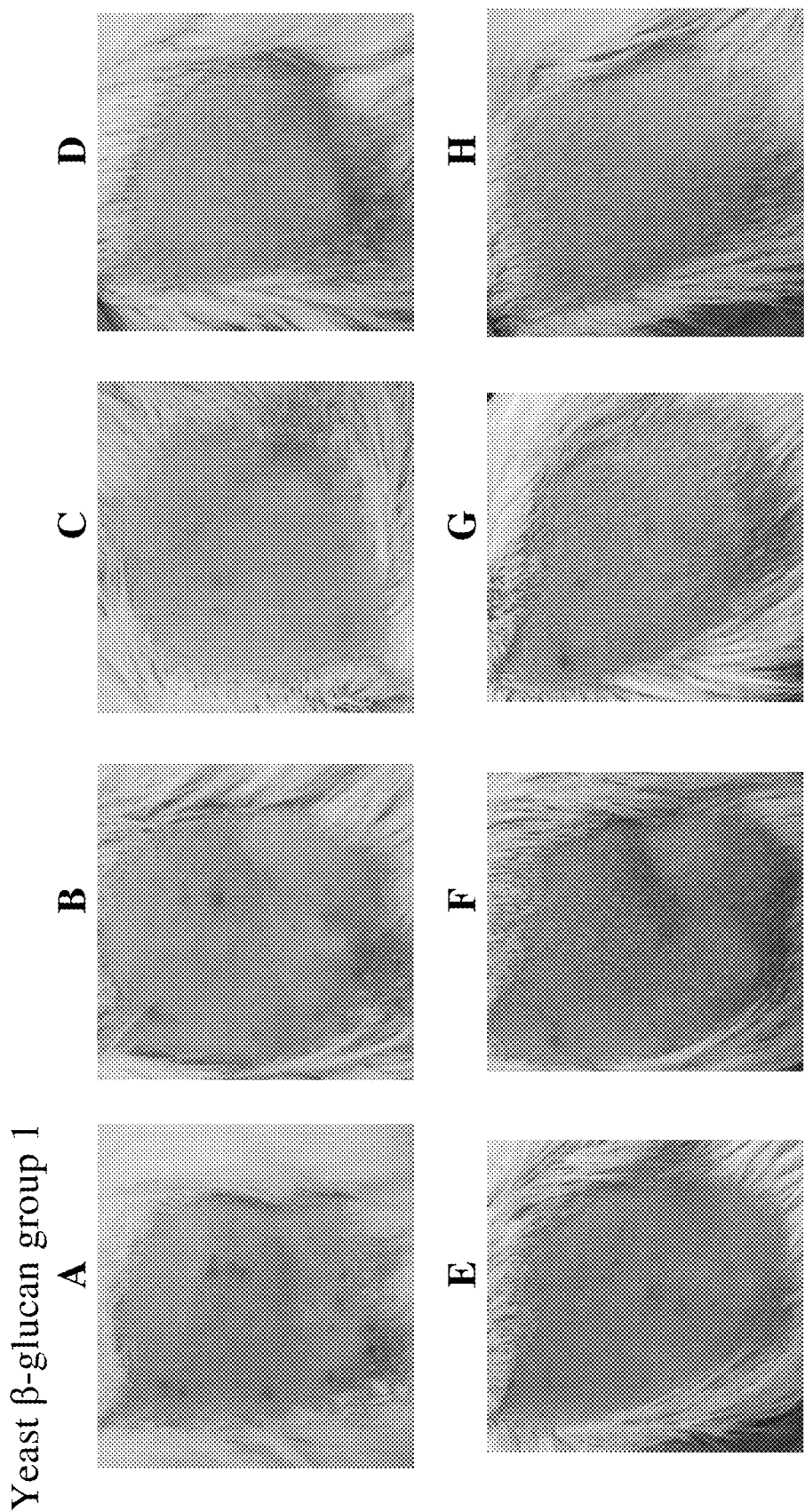
FIG. 10 shows the changes of skin inflammation in guinea pigs of the 0.2% soluble yeast β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 11:
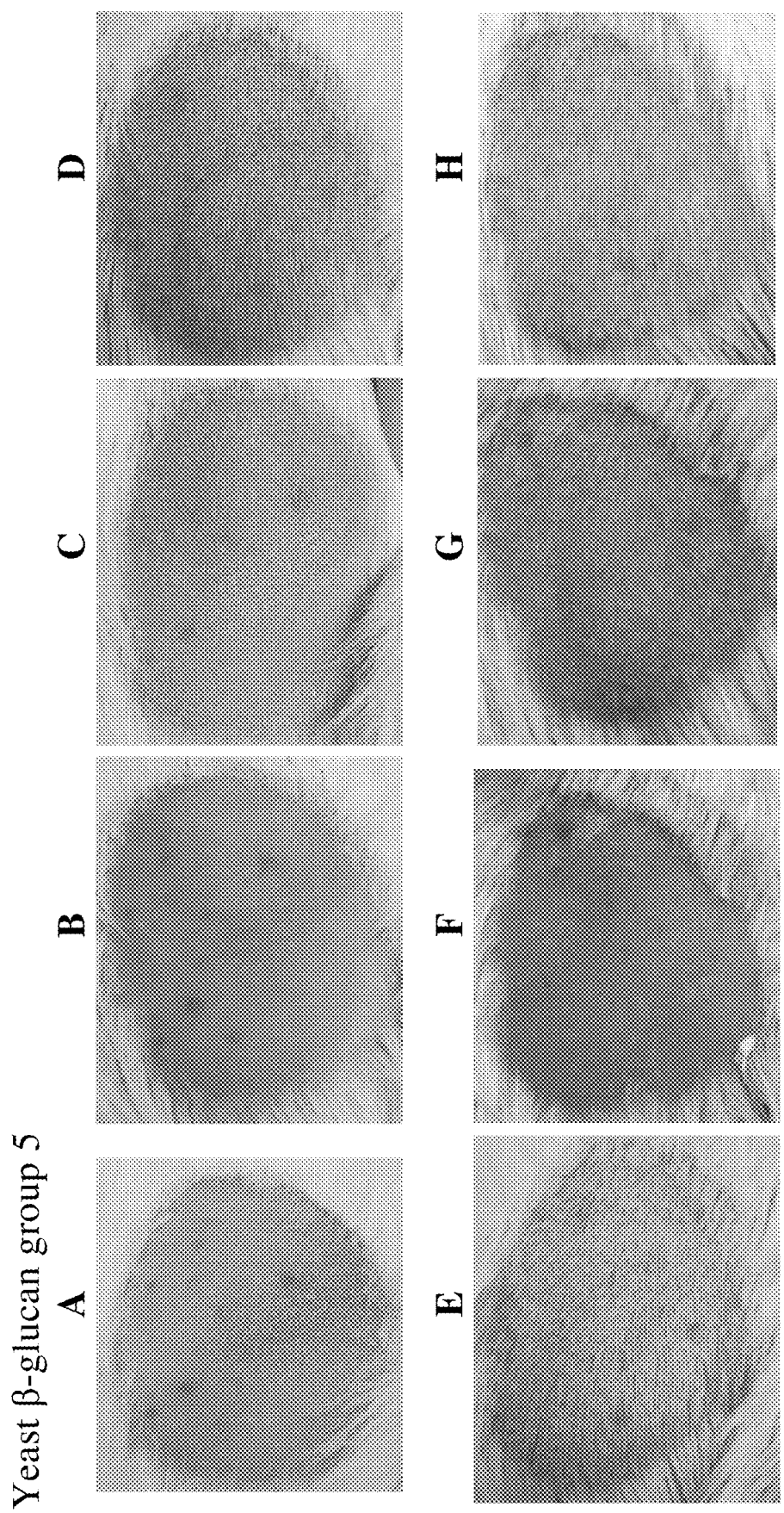
FIG. 11 shows the changes of skin inflammation in guinea pigs of the 0.1% soluble yeast β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 12:
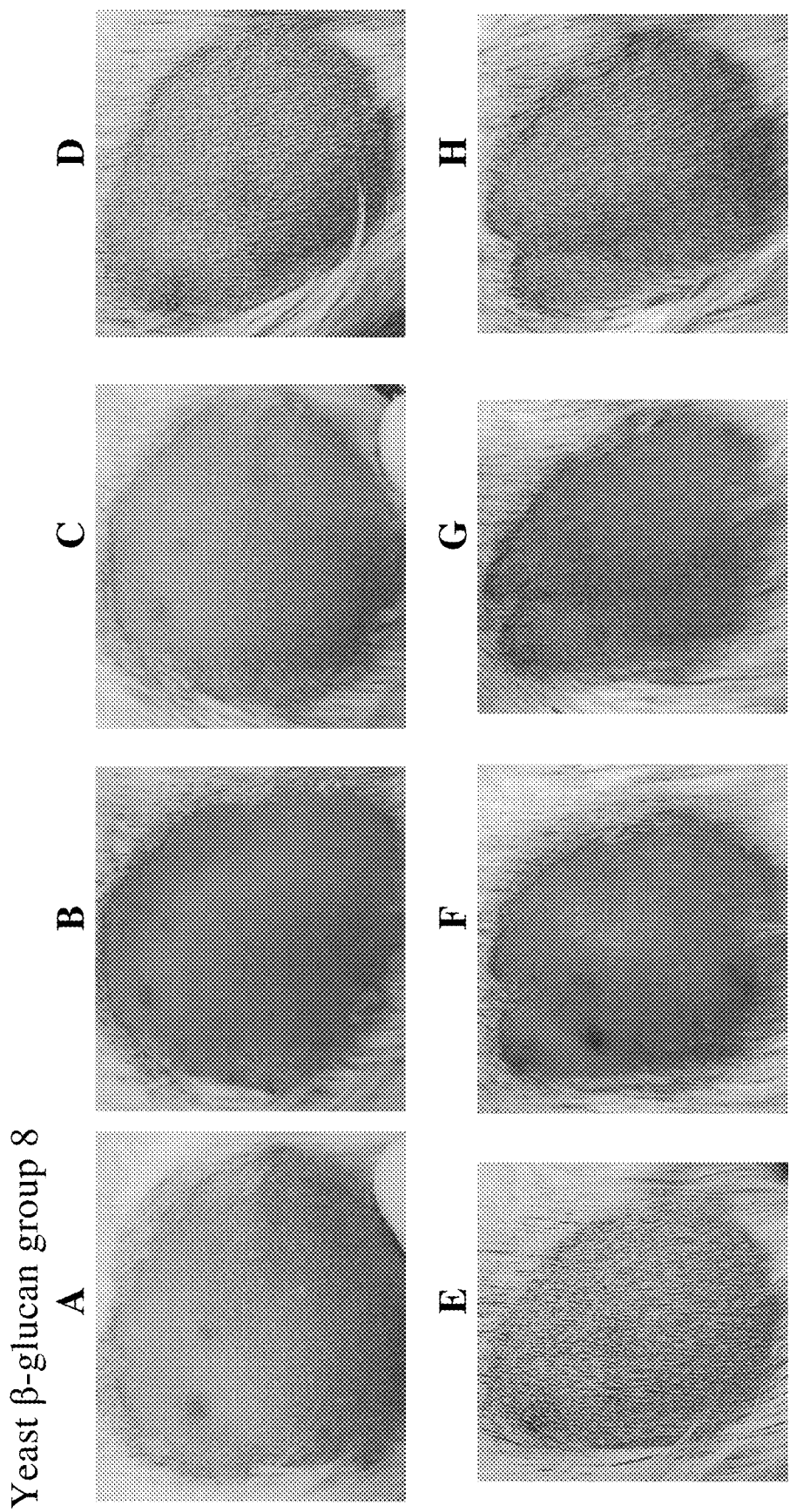
FIG. 12 shows the changes of skin inflammation in guinea pigs of the 0.05% soluble yeast β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 13:
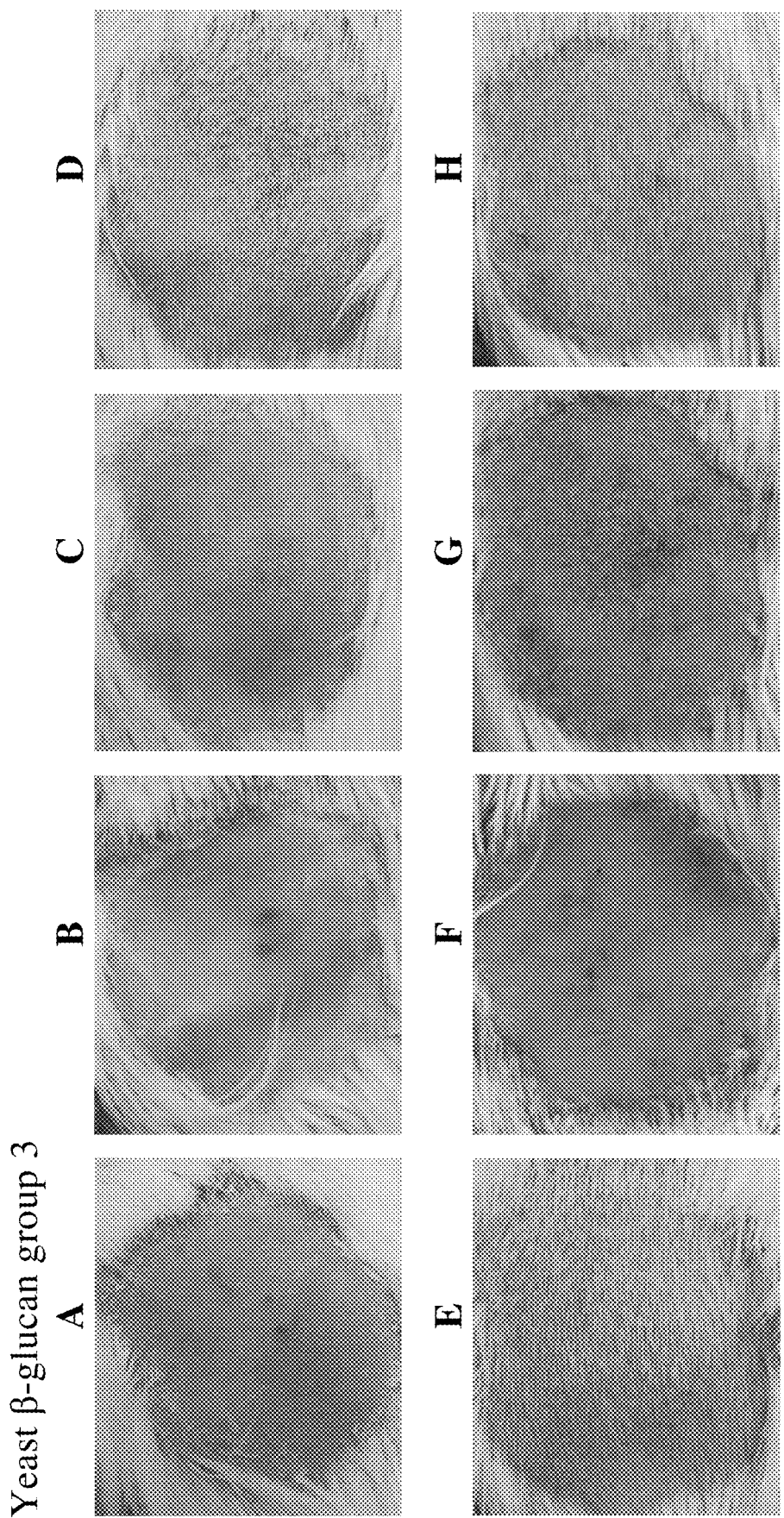
FIG. 13 shows the changes of skin inflammation in guinea pigs of the 0.02% soluble yeast β-glucan treatment group in Example 3 and Example 4 from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 14:
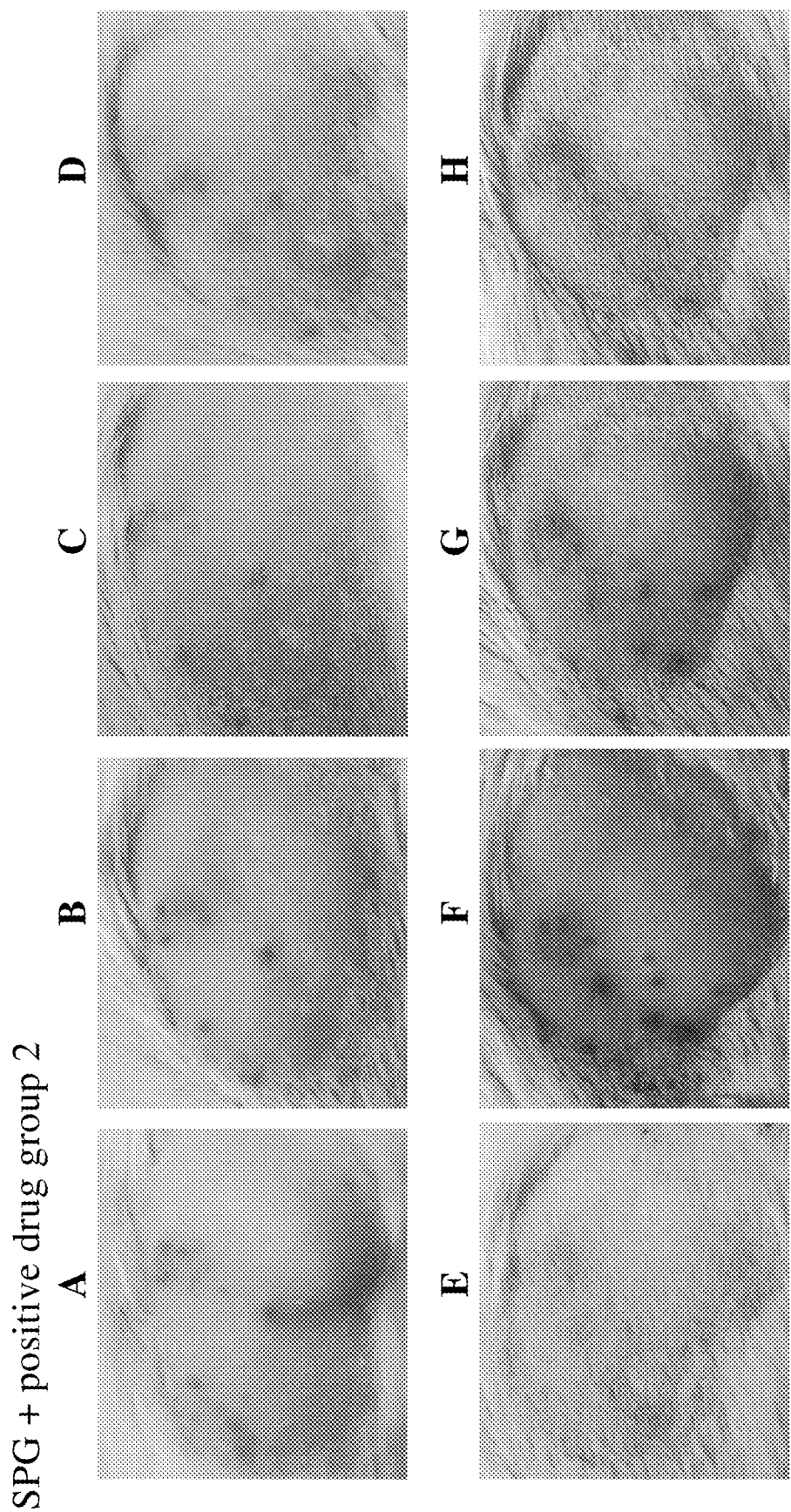
FIG. 14 shows the changes of skin inflammation in guinea pigs of the *Schizophyllum commune* β-glucan combined with positive drug group in Example 3 and Example 4, from the 7th day after stopping applying clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 15:
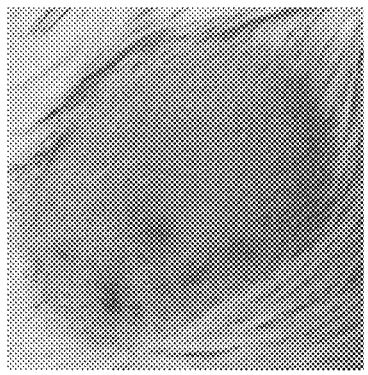
FIG. 15 shows the changes of skin inflammation in guinea pigs of the soluble yeast β-glucan combined with positive drug group in Example 3 and Example 4, from the 7th day after stopping clobetasol propionate solution. A is before treatment (the 7th day after stopping hormone application), and B, C, D, E, F, G and H are the 2nd, 3rd, 4th, 5th, 6th, 7th and 8th day of treatment, respectively.
Figure 15:
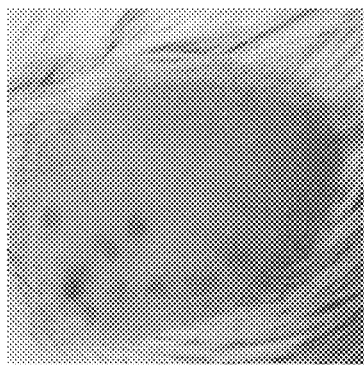
Figure 15:
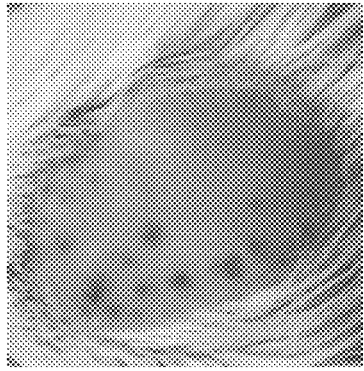
Figure 15:
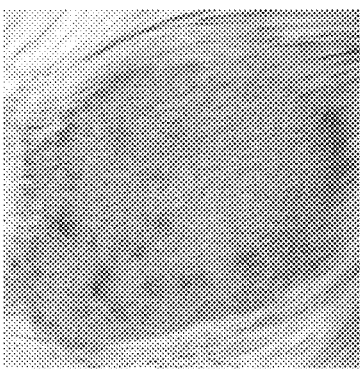
Figure 15:
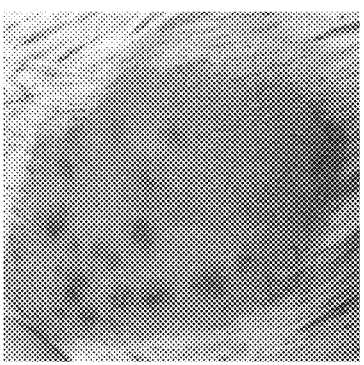
Figure 15:
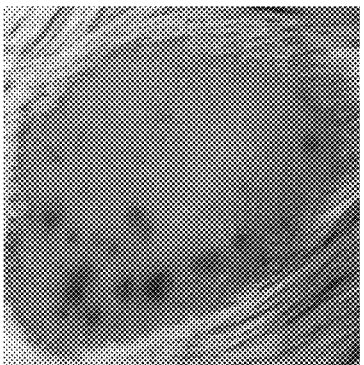
Figure 15:
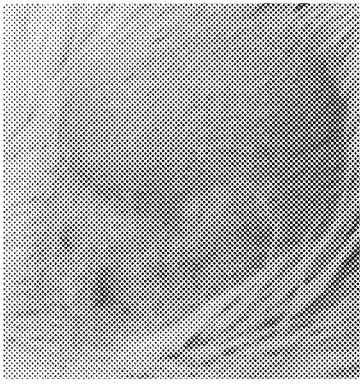

In the *Schizophyllum commune* β-glucan combined with positive drugs group (FIG. 14A-D) and soluble yeast β-glucan combined with positive drugs group (FIG. 15A-D), the degrees of improvement of hormone-dependent dermatitis symptoms such as papules are lower than that when the two β-glucans were used alone, probably due to the side effects of the positive drug, but side effects such as edema caused by the positive drug are significantly suppressed (FIGS. 5, 14, 15, F-H in each figure). Subsequent treatment with both glucan creams resulted in effective control of the inflammatory condition.

Example 4: Relapse Preventive Effect of β-Glucan on Hormone-Dependent Dermatitis Guinea pigs in Example 3 were used, the therapeutic drugs in Table 5 were continued to be applied twice a day when their hormone-dependent dermatitis were effectively controlled, and the preventive effects of β-glucan on the recurrence of hormone-dependent dermatitis were observed.

The daily trend in FIG. 5 shows that the positive drug pimecrolimus does not have any preventive effect on the recurrence of hormone-dependent dermatitis and instead, the severity of the inflammation is worse than when it first occurs due to severe side effects such as edema (FIG. 5E-H).

The hormone-dependent dermatitis of both two β-glucans alone group were cured after one to three recurrences (FIGS. 6-9, E-H of each figure, and FIGS. 10-13, E-H of each figure) and did not recur. Both two β-glucans have different degrees of preventive effects on the recurrence of hormone-dependent dermatitis.

In both β-glucan combined with positive drug groups, the severity at first recurrence were greater than that at first occurrence (FIG. 14F, FIG. 15F), and combined with the data from the positive drug alone group, in this example, these two groups were changed to be treated with β-glucan cream alone. The hormone-dependent dermatitis were effectively controlled in the 0.1% *Schizophyllum commune* β-glucan treatment group after two recurrent episodes and in the 0.1% soluble yeast β-glucan treatment group after three recurrent episodes.

Both β-glucans have preventive effects on the recurrence of hormone-dependent dermatitis and could improve the side effects caused by positive drugs, wherein the effects of *Schizophyllum commune* β-glucan are superior to that of soluble yeast β-glucan.

Example 5: Skin Care Products for Anti-Hormone Dependent Dermatitis

This Example provides 7 skin care products such as anti-hormone dependent dermatitis serum, and the formulations of skin care products for anti-hormone dependent dermatitis are shown in Table 6.

TABLE 6

Formulations of anti-hormone dependent dermatitis skin care products with β-glucan as the main effective ingredient

| | Amount (%) | | | | | | |
|---|---|---|---|---|---|---|---|
| Ingredient | Formulation 1 | Formulation 2 | Formulation 3 | Formulation 4 | Formulation 5 | Formulation 6 | Formulation 7 |
| β-glucan | 0.2 | 0.1 | 0.05 | 0.3 | 0.2 | 0.2 | 0.15 |
| 1,3-Butanediol | 3 | 3 | 2 | 5 | 3 | 2 | 2 |
| 1,3-Propanediol | 2 | 2 | 3 | 3 | 2 | 3 | 3 |
| Allantoin | 2 | 3 | 2 | 0.5 | 2 | 2 | 3 |
| polyethylene glycol 400 | 2 | 2 | 1 | 2 | 1 | 2 | 1 |
| Glycerin | 0.5 | 2 | 2 | 2 | 1 | 1 | 0.5 |
| Water-soluble silicone oil | 0 | 0 | 0 | 2 | 0 | 0 | 0 |
| Caprylic/capric triglycerides | 0 | 0 | 0 | 1 | 0 | 0 | 0 |
| Peony root/bark extract | 0 | 0.3 | 0 | 0.2 | 0 | 0.3 | 0 |
| Flos Chrysanthemi Indici Extract | 0 | 0.2 | 0.3 | 0.1 | 0 | 0 | 0 |

TABLE 6-continued

Formulations of anti-hormone dependent dermatitis skin care
products with β-glucan as the main effective ingredient

| Ingredient | Amount (%) | | | | | | |
|---|---|---|---|---|---|---|---|
| | Formulation 1 | Formulation 2 | Formulation 3 | Formulation 4 | Formulation 5 | Formulation 6 | Formulation 7 |
| Hyaluronic Acid | 0.1 | 0.1 | 0.2 | 0 | 0 | 0.1 | 0.2 |
| copper peptide | 0 | 0 | 0.01 | 0.01 | 0 | 0.01 | 0 |
| Silver | 0 | 0 | 0 | 0 | 0.0008 | 0 | 0.0004 |
| Deionized water | 92.2 | 89.3 | 89.44 | 82.39 | 90.3 | 90.39 | 92.65 |

The skin care products such as the anti-hormone dependence dermatitis serum and the like are prepared according to Table 6 and were applied directly to the facial skin in the morning and evening after cleansing. On average, the products were applied twice a day for 8 weeks, and the trial effects were evaluated.

Example 6: Case Analysis of the Effect of β-Glucan Trialed in Patients with Hormone-Dependent Dermatitis Several cases of hormone-dependent dermatitis patients applied β-glucan and also achieved unexpected effects.

(1) A 47-year-old female patient A, long-term use of cosmetics containing hormones caused hormone-dependent dermatitis with facial redness, swelling and ulceration, accompanied with infection. After 1-year treatment by the dermatology department of a 3A grade hospital and the use of cosmetics that repairing the barrier recommended by the hospital, the infection condition was controlled, but the facial redness and ulceration were not effectively treated. After 1-month use of the skin care serum of Formulation 1 in Example 5, the feedback is that the redness and swelling, and ulceration were controlled, and only the scars resulted from long-term skin lesions remained.

Figure 16:
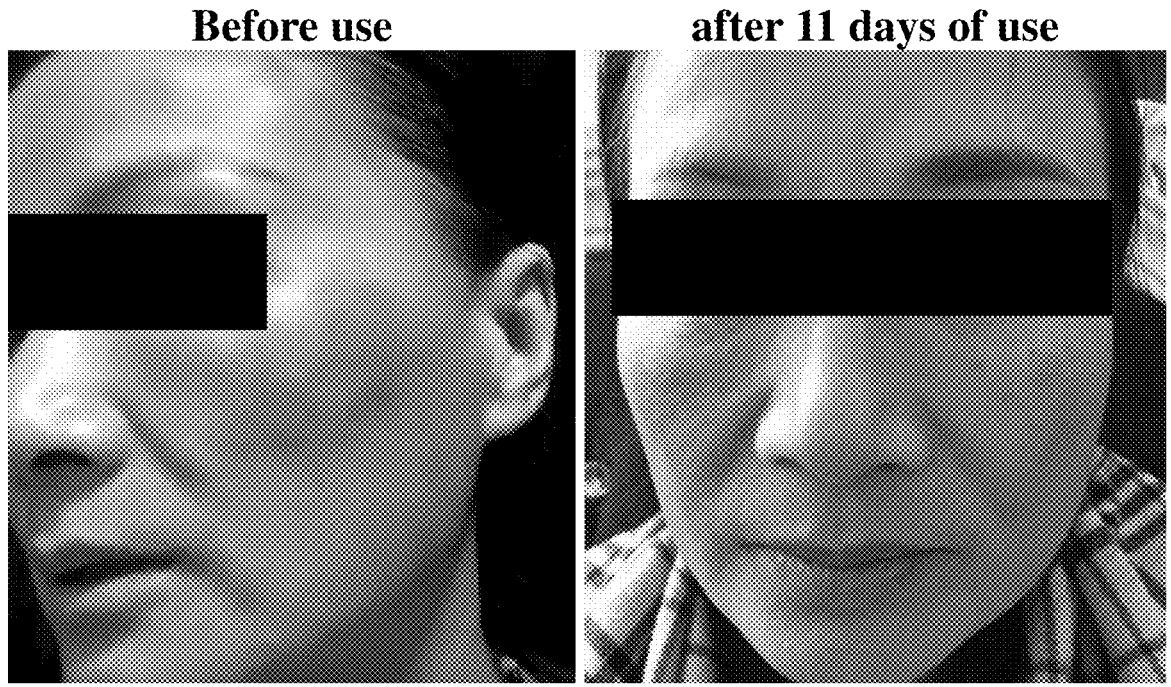
FIG. 16 shows a comparison of the effects of patient B in Example 6 before and after the trial of the *Schizophyllum commune* β-glucan product.

(2) A 48-year-old female patient B, long-term use of hormone-containing cosmetics caused hormone-dependent dermatitis with facial skin redness, swelling and itching, and any other skin care products can not be used anymore. 5 mg/mL of *Schizophyllum commune* β-glucan prepared by the method of Example 1 was used for skin cleansing and skin care (5 mg/mL of *Schizophyllum commune* β-glucan was diluted 20 times with water, and then used for skin cleansing; 5 mg/mL of *Schizophyllum commune* β-glucan was diluted 5 times with water, and then used for daily skin care). After 11 days of trial, the facial swelling was subsided, no itching, and the skin tone returned to normal (FIG. 16)

Figure 17:
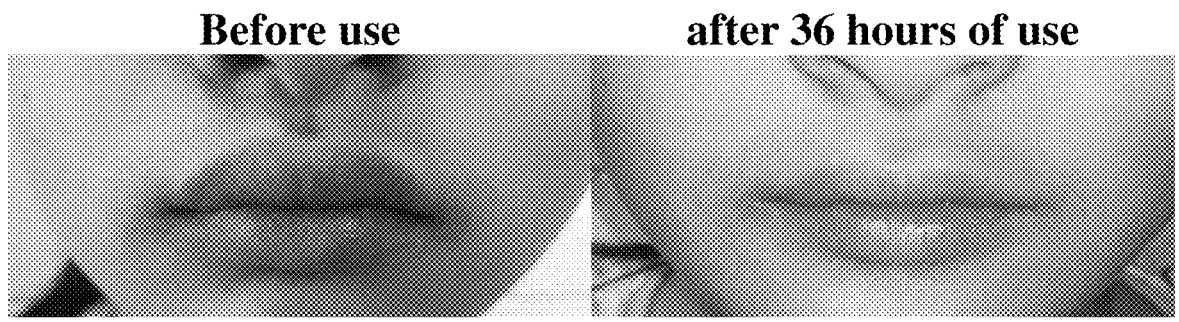
FIG. 17 shows a comparison of the effects of patient C in Example 6 before and after the trial of the *Schizophyllum commune* β-glucan product.

(3) A 10-year-old girl patient C, who relied heavily on lip balm, after continuously use of lip balm several times (6-8 times) a day for 6 months, due to parents' not purchasing it in time, she feel of burning pain on the lips, and the above symptoms subsided after using lip balm again. After that, the parents asked her to stop using the lip balm, and 1 day later, it was found that there were redness and swelling on the lip, papule-like bumps on both upper and lower lips, and purulent papules on the left lower lip corner (FIG. 17 left). 5 mg/mL of sterile *Schizophyllum commune* β-glucan (no preservative) prepared according to the method of Example 1 was used and applied directly to the lips. To prevent bacterial contamination of *Schizophyllum commune* β-glucan, use one tube (25 mL) per day. After 36 h of application, the redness and swelling of the lips subsided, and the pimples on the lips and corners of the mouth disappeared (FIG. 17 right). Half a month later, she used lip balm again for 2 days due to feeling dry and not realizing the severity of the problem, her lips became redness and swelling, and dry and cracked again after stopping the use of the lip balm under her parents' request. After using 5 mg/mL sterile *Schizophyllum commune* β-glucan and Lanolin oil for 2 days, peeling of the lips occurred. Then the use of Lanolin oil was stopped and only 5 mg/mL of sterile *Schizophyllum commune* β-glucan was topically applied several times a day, and the redness and swelling subsided after 2 days. Then the β-glucan was used for another 1 month for consolidating, the symptoms were not recurrence.

Figure 18:
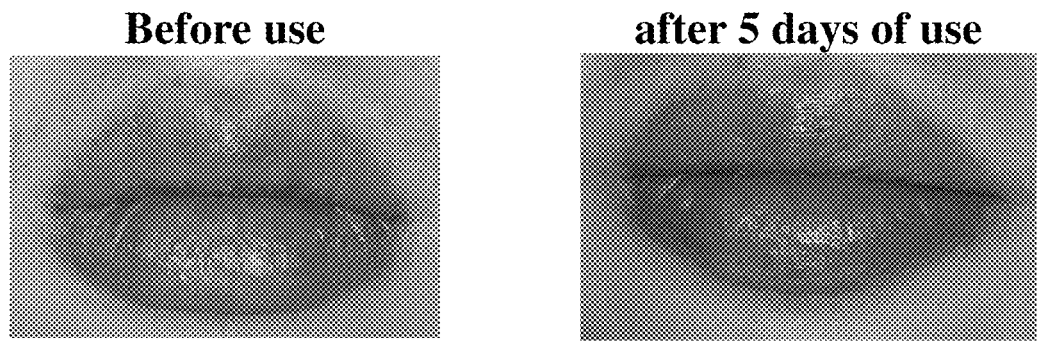
FIG. 18 shows a comparison of the effects of patient D in Example 6 before and after the trial of the *Schizophyllum commune* β-glucan product.

(4) A 19-year-old girl D, a patient with cheilitis, frequent (average 2-3 months) relapsed lip redness and swelling, peeling and papules (FIG. 18). After diagnosis by the dermatology department of a 3A grade hospital, Prednisone Acetate tablets and Compound Glycyrrhizin tablets were orally administered and Tacrolimus ointment was topically applied. Along with the above mentioned drugs, this volunteer used 5 mg/mL of sterile *Schizophyllum commune* β-glucan (without preservative) prepared according to the method of Example 1 and applied it directly to the lips. To prevent bacterial contamination of *Schizophyllum commune* β-glucan, use one tube (25 mL) per day. The redness and swelling subsided after continuous using for 3 days, and the lips stopped peeling after continuous using for 1 month, and after continuous using for 2 months, the application was stopped. At the return visit six months later, the status was stable and no further cheilitis had occurred.

DISCUSSION

The present invention discovers for the first time that β-glucan has significant therapeutic and preventive efficacy against hormone-dependent dermatitis, especially *Schizophyllum commune* β-glucan with high-viscosity and high molecular weight prepared in Example 1 of the present invention.

The present invention found that the therapeutic and preventive activities of β-glucan for hormone-dependent dermatitis are related to its branching degree, the number of glucose in the side chain, steric structure, and molecular weight. Biopolysaccharides without branching degree have no therapeutic and preventive activity for hormone-dependent dermatitis, or are less effective.

Yeast glucan has a variable branching degree, with side chains consisting of β-1,6-glycosidic bonds randomly extending from the main chain, and the number of glucose in the side chains is large and variable, with the large number can be up to hundreds. Granular yeast glucan has long side chain length and easily forms a tight mesh structure, while soluble yeast β-glucan undergoes structural modification and its original activity is greatly affected, which is less effective than *Schizophyllum commune* β-glucan in the treatment and prevention of hormone-dependent dermatitis.

*Schizophyllum commune* β-glucan has a moderate degree of branching, with only one glucose residue in the side chain, as well as has a high molecular weight and a larger and longer three-dimensional triple helix structure, which has good therapeutic and preventive activities against hormone-dependent dermatitis.

All documents referred to in the present invention are incorporated by reference herein as if each document were individually incorporated by reference. Further, it should be understood that upon reading the foregoing lecture of the present invention, various modifications or modifications may be made to the present invention by those skilled in the art, the equivalents of which also fall within the scope defined by the appended claims of the present application.

The invention claimed is:

1. A method for treating hormone-dependent dermatitis comprising a step of administering ß-glucan to a subject in need thereof; wherein β-glucan is *Schizophyllum commune* β-glucan, and the molecular weight of the β-glucan is 3000-6000 kD;
   wherein the hormone-dependent dermatitis is caused by the long-term incorrect use of drug or cosmetic containing a glucocorticoid.

2. The method of claim 1, wherein the molecular weight of the β-glucan is 3000-5000 kD.

3. The method of claim 1, wherein the treating hormone-dependent dermatitis comprises: improving or alleviating symptoms of hormone-dependent dermatitis, or accelerating regression or healing of hormone-dependent dermatitis, or improving scars caused by hormone-dependent dermatitis, or accelerating regression of scars caused by hormone-dependent dermatitis.

4. The method of claim 1, wherein the β-glucan is administered as a formulation or composition, wherein the formulation or composition comprises (a) the β-glucan; and (b) pharmaceutically, or cosmetically acceptable carriers or excipients.

* * * * *